(12) United States Patent
Patel et al.

(10) Patent No.: US 6,573,054 B2
(45) Date of Patent: *Jun. 3, 2003

(54) QUANTITATIVE DETERMINATION OF NUCLEIC ACID AMPLIFICATION PRODUCTS

(75) Inventors: Rajesh Patel, Fremont, CA (US); Nurith Kurn, Palo Alto, CA (US)

(73) Assignee: Dade Behring Inc., Deerfield, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/043,415

(22) Filed: Jan. 10, 2002

(65) Prior Publication Data

US 2002/0182620 A1 Dec. 5, 2002

Related U.S. Application Data

(63) Continuation of application No. 09/025,639, filed on Feb. 18, 1998, now Pat. No. 6,365,346.

(51) Int. Cl.[7] .............................. C12Q 1/68; C12Q 1/66; G01N 33/53; C12P 19/34; C07H 21/04
(52) U.S. Cl. ..................... 435/6; 435/7; 435/8; 435/28; 435/91; 536/24.3
(58) Field of Search .............................. 435/6, 7, 8, 28, 435/91; 536/24.3

(56) References Cited

U.S. PATENT DOCUMENTS

| | | | | |
|---|---|---|---|---|
| 4,193,983 A | | 3/1980 | Ullman et al. | |
| 4,766,062 A | | 8/1988 | Diamond et al. | |
| 4,853,327 A | * | 8/1989 | Dattagupta et al. | 435/6 |
| 4,868,104 A | | 9/1989 | Kurn et al. | |
| 4,891,324 A | | 1/1990 | Pease et al. | |
| 5,017,473 A | | 5/1991 | Wagner | |
| 5,030,557 A | * | 7/1991 | Hogan et al. | 435/6 |
| 5,219,727 A | * | 6/1993 | Wang et al. | 435/6 |
| 5,340,716 A | | 8/1994 | Ullman et al. | |
| 5,409,818 A | * | 4/1995 | Davey et al. | 435/91.21 |
| 5,474,895 A | | 12/1995 | Ishii et al. | |
| 5,573,907 A | | 11/1996 | Carrino et al. | |
| 5,593,867 A | * | 1/1997 | Walker et al. | 435/91.2 |
| 5,624,803 A | | 4/1997 | Noonberg et al. | |
| 5,635,347 A | * | 6/1997 | Link et al. | 435/6 |
| 5,635,352 A | | 6/1997 | Urdea et al. | |
| 5,656,207 A | | 8/1997 | Woodhead et al. | |
| 5,665,547 A | | 9/1997 | Pardee et al. | |
| 5,834,255 A | | 11/1998 | Van Gemen et al. | |
| 5,849,489 A | * | 12/1998 | Heller | |
| 5,888,729 A | * | 3/1999 | Kacian et al. | 435/6 |
| 6,365,346 B1 | * | 4/2002 | Patel et al. | |

FOREIGN PATENT DOCUMENTS

| | | | |
|---|---|---|---|
| EP | 0 345 776 A2 | * | 12/1989 |
| EP | 450370 A1 | | 3/1991 |
| EP | 0 525 882 A1 | * | 2/1993 |
| EP | WO 94/03812 | * | 2/1994 |
| EP | 0 623 682 A1 | * | 11/1994 |
| EP | WO 95/08644 | * | 3/1995 |
| WO | 345776 B1 | * | 12/1989 |
| WO | 515194 A2 | * | 11/1992 |
| WO | WO 9310267 | | 5/1993 |
| WO | WO 94/03812 | * | 2/1994 |
| WO | WO 94/04706 | * | 3/1994 |
| WO | WO 9406937 | | 3/1994 |
| WO | WO 9728279 | | 8/1997 |

OTHER PUBLICATIONS

Mehrpouyan et al., "A rapid and sensitive method for non–isotopic quantitation of HIV–1 RNA using thermophilic SDA and flow cytometry", Molecular and Cellular Probes (1997), vol. 11, pp. 337–347, Jul. 1997.* van Gemen et al., "A one–tube quantitative HIV–1 RNA NASBA nucleic acid amplification assay using ECL labelled probes", J. Virological Methods, vol. 49, pp. 157–168, Feb. 1994.*

WO 94/US10732 9401921 (Duplicate of WO 9508644A1), Europe, filed Mar. 30, 1995.*

(List continued on next page.)

Primary Examiner—W. Gary Jones
Assistant Examiner—Arun K. Chakrabarti
(74) Attorney, Agent, or Firm—Patrick G. Gattari; Cynthia G. Tymeson

(57) ABSTRACT

The present invention relates to a method for detecting the amount of a target polynucleotide in a sample. A combination is provided in a medium. The combination comprises (i) a sample suspected of containing the target polynucleotide, the target polynucleotide being in single stranded form, (ii) a reference polynucleotide comprising a sequence that is common with a sequence of the target polynucleotide, and (iii) a predetermined amount of an oligonucleotide probe that has a sequence that hybridizes with the sequence that is common. The combination is subjected to conditions for amplifying the target polynucleotide and the reference polynucleotide. The conditions permit formation of substantially non-dissociative complexes of the target polynucleotide and the reference polynucleotide, respectively, with the oligonucleotide probe. Furthermore, the predetermined amount of the oligonucleotide probe is less than the expected amount of the amplified target polynucleotide. The ratio of the amount of the complex of the target polynucleotide with the oligonucleotide probe to the amount of the complex of the reference polynucleotide with the oligonucleotide probe is determined. Determination of the ratio is facilitated by employing second and third oligonucleotide probes. The second oligonucleotide probe has a sequence that hybridizes only with the second sequence of the target polynucleotide. The third oligonucleotide probe has a sequence that hybridizes only with a respective second sequence of the reference polynucleotide. The ratio is related to the known amount of the reference polynucleotide to determine the amount of the target polynucleotide in the sample. One or more reference polynucleotides may be employed with a corresponding third oligonucleotide probe for each reference probe. Kits for carrying out the above methods are also disclosed. The method is particularly applicable to the amplification and detection of RNA.

22 Claims, 2 Drawing Sheets

OTHER PUBLICATIONS

WO 97/21832 (Equivalent to WO 96/EP5472 961206, Europe, filed Jun. 19, 1997.*

WO 93/16194 (Equivalent to DE 4234086A1), Europe, filed Aug. 19, 1993.*

Gudibande et al; *Molecular and Cellular Probes; 6: 495–503*; Rapid, Non–Separation Electrochemiluminescent DNA Hybridization Assays for PCR Productes, Using 3'–Labelled Oligonucleotide Probes; 1992.*

Solomon et al; *J. Org. Chem.; 58:2232–2243*; Chemical Synthesis and Characterization of Duplex DNA Containing a New Base Pair: A Nondisruptive, Benzofused Pyrimidine Analog; 1993.*

Marmaro et al; *Abstract, Clinical Chem.*;41 (11):1685; (1995); A TaqMan™ Multiplex PCR mRNA Quantitation Assay.*

Matsuoka; *Rinsho Kensa*; 35 (6);627–31; (1991); Hybridization Protection Assay.*

Tyagi, et al., *Nat. Biotechnol.*; (1996)14(3):303–308; Molecular Beacons: probes that Fluoresce upon Hybridization.* vanGemen, et al.: *Journal of Virological Methods*; A one–tube quantitative HIV–1 RNA NASBA nucleic acid amplification assay using electorchemiluminescent (ECL) labelled probes; 49; 157–168; 1994.*

Ullman, et al.; *Clin Chem*; Luminescent oxygen channeling assay (LOCI™): sensitive, broadly applicable homogeneous immunoassay method; 42:9; 1518–1626; 1996.*

Mehrpouyan et al., "A rapid and sensitive method non–isotopic quantitation of HIV–1 RNA using thermophilic SDA and flow cytometry", Molecular and Cellular Probes (1997), vol. 11, pp. 337–347.*

* cited by examiner

SEQUENCE LISTING

```
<160> NUMBER OF SEQ ID NOS: 8

<210> SEQ ID NO 1
<211> LENGTH: 45
<212> TYPE: DNA
<213> ORGANISM: Artificial Sequence
<220> FEATURE:
<221> NAME/KEY: misc_binding
<222> LOCATION: (1)...(45)
<223> OTHER INFORMATION: Synthetic DNA Probe

<400> SEQUENCE: 1
tttttttttt tttttttttt tgttaaaaga gaccatcaat gagga            45

<210> SEQ ID NO 2
<211> LENGTH: 38
<212> TYPE: DNA
<213> ORGANISM: Artificial Sequence
<220> FEATURE:
<221> NAME/KEY: misc_binding
<222> LOCATION: (1)...(38)
<223> OTHER INFORMATION: Synthetic DNA Probe

<400> SEQUENCE: 2
tacttactta cttacttact gctgcagaat gggataga                    38

<210> SEQ ID NO 3
<211> LENGTH: 38
<212> TYPE: DNA
<213> ORGANISM: Artificial Sequence
<220> FEATURE:
<221> NAME/KEY: misc_binding
<222> LOCATION: (1)...(38)
<223> OTHER INFORMATION: Synthetic DNA Probe

<400> SEQUENCE: 3
gatgacagtc gcatgcagct atctatctat ctatctat                    38

<210> SEQ ID NO 4
<211> LENGTH: 24
<212> TYPE: DNA
<213> ORGANISM: Artificial Sequence
<220> FEATURE:
<221> NAME/KEY: misc_binding
<222> LOCATION: (1)...(24)
<223> OTHER INFORMATION: Synthetic DNA Probe

<400> SEQUENCE: 4
aaaaaaaaaa aaaaaaaaaa aaaa                                   24

<210> SEQ ID NO 5
<211> LENGTH: 24
<212> TYPE: DNA
<213> ORGANISM: Artificial Sequence
<220> FEATURE:
<221> NAME/KEY: misc_binding
<222> LOCATION: (1)...(24)
<223> OTHER INFORMATION: Synthetic DNA Probe

<400> SEQUENCE: 5
atagatagat agatagatag atag                                   24

<210> SEQ ID NO 6
<211> LENGTH: 24
<212> TYPE: DNA
<213> ORGANISM: Artificial Sequence
```

```
<220> FEATURE:
<221> NAME/KEY: misc_binding
<222> LOCATION: (1)...(24)
<223> OTHER INFORMATION: Synthetic DNA Probe

<400> SEQUENCE: 6
atgaatgaat gaatgaatga atga                                    24

<210> SEQ ID NO 7
<211> LENGTH: 38
<212> TYPE: DNA
<213> ORGANISM: Artificial Sequence
<220> FEATURE:
<221> NAME/KEY: misc_binding
<222> LOCATION: (1)...(38)
<223> OTHER INFORMATION: Synthetic DNA Probe

<400> SEQUENCE: 7
gctgcagaat gggatagata cttacttact tacttact                     38

<210> SEQ ID NO 8
<211> LENGTH: 39
<212> TYPE: DNA
<213> ORGANISM: Artificial Sequence
<220> FEATURE:
<221> NAME/KEY: misc_binding
<222> LOCATION: (1)...(39)
<223> OTHER INFORMATION: Synthetic DNA Probe

<400> SEQUENCE: 8
gctgcagaca gtgtagatac tatctatcta tctatctat                    39
```

QUANTITATIVE DETERMINATION OF NUCLEIC ACID AMPLIFICATION PRODUCTS

This application is a continuation of U.S. Ser. No. 09/025,639 which was filed on Feb. 18, 1998 now U.S. Pat. No. 6,365,346.

BACKGROUND OF THE INVENTION

1. Field of the Invention

Significant morbidity and mortality are associated with infectious diseases. More rapid and accurate diagnostic methods are required for better monitoring and treatment of disease. Molecular methods using DNA probes, nucleic acid hybridizations and in vitro amplification techniques are promising methods offering advantages to conventional methods used for patient diagnoses.

Nucleic acid hybridization has been employed for investigating the identity and establishing the presence of nucleic acids. Hybridization is based on complementary base pairing. When complementary single stranded nucleic acids are incubated together, the complementary base sequences pair to form double stranded hybrid molecules. The ability of single stranded deoxyribonucleic acid (ssDNA) or ribonucleic acid (RNA) to form a hydrogen bonded structure with a complementary nucleic acid sequence has been employed as an analytical tool in molecular biology research. The availability of radioactive nucleoside triphosphates of high specific activity and the $^{32}P$ labeling of DNA with T4 polynucleotide kinase has made it possible to identify, isolate, and characterize various nucleic acid sequences of biological interest. Nucleic acid hybridization has great potential in diagnosing disease states associated with unique nucleic acid sequences. These unique nucleic acid sequences may result from genetic or environmental change in DNA by insertions, deletions, point mutations, or by acquiring foreign DNA or RNA by means of infection by bacteria, molds, fungi, and viruses. Nucleic acid hybridization has, until now, been employed primarily in academic and industrial molecular biology laboratories. The application of nucleic acid hybridization as a diagnostic tool in clinical medicine is limited because of the frequently very low concentrations of disease related DNA or RNA present in a patient's body fluid and the unavailability of a sufficiently sensitive method of nucleic acid hybridization analysis.

One method for detecting specific nucleic acid sequences generally involves immobilization of the target nucleic acid on a solid support such as nitrocellulose paper, cellulose paper, diazotized paper, or a nylon membrane. After the target nucleic acid is fixed on the support, the support is contacted with a suitably labeled probe nucleic acid for about two to forty-eight hours. After the above time period, the solid support is washed several times at a controlled temperature to remove unhybridized probe. The support is then dried and the hybridized material is detected by autoradiography or by spectrometric methods.

When very low concentrations must be detected, the above method is slow and labor intensive, and nonisotopic labels that are less readily detected than radiolabels are frequently not suitable.

Recently, a method for the enzymatic amplification of specific segments of DNA known as the polymerase chain reaction (PCR) method has been described. This in vitro amplification procedure is based on repeated cycles of denaturation, oligonucleotide primer annealing, and primer extension by thermophilic polymerase, resulting in the exponential increase in copies of the region flanked by the primers. The PCR primers, which anneal to opposite strands of the DNA, are positioned so that the polymerase catalyzed extension product of one primer can serve as a template strand for the other, leading to the accumulation of a discrete fragment whose length is defined by the distance between the 5' ends of the oligonucleotide primers.

Other methods for amplifying nucleic acids have also been developed. These methods include single primer amplification, ligase chain reaction (LCR), nucleic acid sequence based amplification (NASBA) and the Q-beta-replicase method. Regardless of the amplification used, the amplified product must be detected.

After amplification of a particular nucleic acid, a separate step is carried out prior to detecting amplified material. The various nucleic acid amplification procedures developed over the past few years greatly enhanced the sensitivity of detecting defined nucleic acid species in a test sample. The frequent formation of non-specific amplification products requires selective detection of the specific amplification product, which is often carried out using multiple probes complementary to regions within the specific amplified sequence.

One method for detecting nucleic acids is to employ nucleic acid probes that have sequences complementary to sequences in the amplified nucleic acid. One method utilizing such probes is described in U.S. Pat. No. 4,868,104. A nucleic acid probe may be, or may be capable of being, labeled with a reporter group or may be, or may be capable of becoming, bound to a support. Detection of signal depends upon the nature of the label or reporter group. If the label or reporter group is an enzyme, additional members of the signal producing system include enzyme substrates and so forth.

Usually, the probe is comprised of natural nucleotides such as ribonucleotides and deoxyribonucleotides and their derivatives although unnatural nucleotide mimetics such as peptide nucleic acids (PNA) and oligomeric nucleoside phosphonates are also used. Commonly, binding of the probes to the target is detected by means of a label incorporated into the probe. Binding can be detected by separating the bound probe from the free probe and detecting the label. For this purpose it is usually necessary to form a sandwich comprised of the labeled probe, the target and a probe that is or can become bound to a surface. Alternatively, binding can be detected by a change in the signal-producing properties of the label upon binding, such as a change in the emission efficiency of a fluorescent or chemiluminescent label. This permits detection to be carried out without a separation step.

Homogeneous methods that have been utilized include the Taqman method used by Roche Molecular Diagnostics. In this approach a probe is used that is labeled with a fluorescer and a quencher. The polymerase used in PCR is capable of cutting the probe when it is bound to the target DNA and causing separation of these labels. Changes in the polarization of fluorescence upon binding of a fluorescer-labeled probe to target DNA are used by Becton Dickenson to detect the formation of DNA in Strand Displacement Amplification (SDA). Binding of two probes, one with a chemiluminescer bead and one with a sensitizer bead has been used by Behring Diagnostics Inc. for detection of DNA produced by PCR and single primer amplification. Binding of an electroluminescent ruthenium labeled probe to a biotinylated target RNA and capture of the complex on magnetic beads has been used by Organon Teknika for detection of RNA produced in NASBA. GenProbe has carried out detection of RNA by means of an acridinium labeled probe that changes chemiluminescence efficiency when the probe is bound to target RNA.

Each of the above methods has limitations. Where two or more probes are required for detection and quantitation of products of specific nucleic acid amplifications, increasing the amount of target increases the signal up to a point and then the signal fall off (the "prozone" phenomenon). In general, loss of signal is realized under the prozone phenomenon when the analyte concentration exceeds probe concentration. Methods that require a capturable ligand in the target cannot be used on non-amplified nucleic acids nor are all amplification methods capable of introducing a ligand into the amplified product. Fluorescence polarization changes on binding are small and the sensitivity is therefore limited. Taqman is subject to problems with emission form the quencher, which limits sensitivity; GenProbe's chemiluminescent probe requires reagent additions prior to detection.

It is desirable to have a sensitive, simple method for amplifying and detecting nucleic acids preferably, in a homogeneous format. The method should minimize the number and complexity of steps and reagents and avoid the prozone phenomenon.

Also, it is desirable to know the concentration of the amplified product in the reaction medium. Quantitation of nucleic acid amplification products has become an important molecular diagnostic tool.

2. Description of the Related Art

Rapid, non-separation electrochemiluminescent DNA hybridization assays for PCR products using 3'-labeled oligonucleotide probes is described by Gudibande, et al., (1992) *Molecular and Cellular Probes*, 6: 495–503. A related disclosure is found in international patent application WO 9508644 A1 (950330).

Marmaro, et al., (Meeting of the American Association of Clinical Chemists, San Diego, Calif., November 1994, Poster No. 54) discusses the design and use of fluorogenic probes in TaqMan, a homogeneous PCR assay.

German patent application DE 4234086-A1 (92.02.05) (Henco, et al.) discusses the determination of nucleic acid sequences amplified in vitro in enclosed reaction zone where probe(s) capable of interacting with target sequence is present during or after amplification and spectroscopically measurable parameters of probe undergo change thereby generating signal.

A process for the determination of nucleic acid molecules at low concentrations by amplification using labeled primers is discussed in patent application WO 96-EP5472 961206 (Eigen, et al.).

A self-sustained sequence replication electrochemiluminescent nucleic acid assay is disclosed in patent application WO 94-US10732 940921 (Kenten, et al.).

A hybridization protection assay is discussed by Matsuoka in *Rinsho Kensa* (1991) 35(6):627–631.

U.S. Pat. No. 5,593,867 (Walker, et al.) discloses a fluorescence polarization detection of nucleic acid amplification using fluorescently labeled oligonucleotide probes and detector-probe extension products.

Molecular beacons: probes that fluoresce upon hybridization are discussed by Tyagi, et al.) in *Nat. Biotechnol.* (1996) 14(3):303–308.

U.S. Pat. No. 5,656,207 (Woodhead, et al.) discloses a method for detecting or quantifying multiple analytes using labelling techniques.

U.S. Pat. No. 5,340,716 (Ullman, et al.) describes an assay method utilizing photoactivated chemiluminescent labels.

Photoactivatable chemiluminescent matrices are described in patent application WO 94/03812 (Pease, et al.).

European Patent Application No. 0 515 194 A2 (Ullman, et al.) discloses assay methods utilizing induced luminescence. The references cited therein are incorporated herein by reference including without limitation U.S. Pat. No. 5,017,473 (Wagner), which discloses a homogeneous chemiluminescence immunoassay using a light absorbing material, European Patent Application No. 0,345,776 (McCapra), which discloses specific binding assays that utilize a sensitizer as a label, U.S. Pat. No. 4,193,983 (Ullman, et al.), which discloses labeled liposome particle compositions and immunoassays therewith, U.S. Pat. No. 4,891,324 (Pease, et al.), which describes a particle with luminescer for assays.

SUMMARY OF THE INVENTION

One embodiment of the present invention is a method for detecting the amount of a target polynucleotide in a sample. A combination is provided in a medium. The combination comprises (i) a sample suspected of containing the target polynucleotide, the target polynucleotide being in single stranded form, (ii) a reference polynucleotide comprising a sequence that is common with a sequence of the target polynucleotide, and (iii) a predetermined amount of an oligonucleotide probe that has a sequence that hybridizes with the sequence that is common. The combination is subjected to conditions for amplifying the target polynucleotide and the reference polynucleotide. The conditions permit formation of substantially non-dissociative complexes of the target polynucleotide and the reference polynucleotide, respectively, with the oligonucleotide probe. Furthermore, the predetermined amount of the oligonucleotide probe is less than the expected amount of the amplified target polynucleotide. The ratio of the amount of the complex of the target polynucleotide with the oligonucleotide probe to the amount of the complex of the reference polynucleotide with the oligonucleotide probe is determined. The ration is related to the known amount of the reference polynucleotide to determine the amount of the target polynucleotide in the sample.

Another aspect of the present invention concerns a method for detecting the amount of a target polynucleotide in a sample. In this aspect a combination is provided in a medium. The combination comprises (i) a sample suspected of containing the target polynucleotide, the target polynucleotide being in single stranded form, (ii) predetermined amounts of one or more reference polynucleotides, each of the reference polynucleotides comprising a first sequence that is common with a first sequence of the target polynucleotide and a second sequence that is different from a second sequence of the target polynucleotide, (iii) a predetermined amount of a first oligonucleotide probe that has a sequence that hybridizes with the sequence that is common, (iv) a second oligonucleotide probe that has a sequence that hybridizes only with the second sequence of the target polynucleotide, and (v) one or more third oligonucleotide probes. Each of the third oligonucleotide probes has a sequence that hybridizes only with a respective second sequence of one of the reference polynucleotide. The combination is subjected to isothermal conditions for amplifying with equal efficiency the target polynucleotide and the one or more reference polynucleotides. The conditions permit formation of a substantially non-dissociative first termolecular complex of the target polynucleotide, the first oligonucleotide probe and the second oligonucleotide probe and a substantially non-dissociative second termolecular complex of each of the reference polynucleotide with the first oligonucleotide probe and a respective third oligonucleotide probe. The predetermined amount of the first oligonucleotide probe is less than the expected amount of the amplified target polynucleotide. A determination is made of the ratio of the amount of the first termolecular complex to the amount of each of the second termolecular complexes. Each of the ratios is related to the predetermined amount of each of the reference polynucleotides to determine the amount of the target polynucleotide in the sample.

Another embodiment of the present invention is a method for detecting the amount of a target polynucleotide in a sample. In this embodiment a combination is provided in a medium. The combination comprises (i) a sample suspected of containing the target polynucleotide, the target polynucleotide being in single stranded form, (ii) predetermined amounts of one or more reference polynucleotides, each of the reference polynucleotides comprising a first sequence that is common with a first sequence of the target polynucleotide and a second sequence that is different from a second sequence of the target polynucleotide, (iii) a predetermined amount of a first oligonucleotide probe that has a sequence that hybridizes with the sequence that is common wherein the first oligonucleotide probe has, or is capable of having, a sensitizer attached thereto, (iv) a second oligonucleotide probe that has a sequence that hybridizes only with the second sequence of the target polynucleotide wherein the second oligonucleotide probe has, or is capable of having, a first chemiluminescent compound attached thereto, and (v) one or more third oligonucleotide probes. Each of the one or more third oligonucleotide probes has a sequence that hybridizes only with a respective second sequence of one of the reference polynucleotide. In addition, each of the third oligonucleotide probes has, or is capable of having, a second chemiluminescent compound attached thereto. The first and the second chemiluminescent compounds differ in signal produced when activated by the photosensitizer. The second chemiluminescent compound is different for each of the third oligonucleotide probes. The combination is subjected to isothermal conditions for amplifying with equal efficiency the target polynucleotide and each of the reference polynucleotide. The conditions permit formation of a substantially non-dissociative first termolecular complex of the target polynucleotide, the first oligonucleotide probe and the second oligonucleotide probe and a substantially non-dissociative second termolecular complex of each of the reference polynucleotides with the first oligonucleotide probe and a respective third oligonucleotide probe. The predetermined amount of the first oligonucleotide probe is less than the expected amount of the amplified target polynucleotide. The ratio of the amount of the signal produced by the first termolecular complex to the amount of signal produced by each of the second termolecular complexes is determined. Each of the ratios is related to the amount of each respective reference polynucleotide to determine the amount of the target polynucleotide in the sample.

Another embodiment of the present invention is a kit for use in amplification and detection of a target polynucleotide. The kit is a packaged combination and comprises reagents for conducting an amplification of the target polynucleotide and predetermined amounts of one or more reference polynucleotides. Each of the reference polynucleotides comprises a first sequence that is common with a first sequence of the target polynucleotide and a second sequence that is different from a second sequence of the target polynucleotide. Also in the kit are a predetermined amount of a first oligonucleotide probe that has a sequence that hybridizes with the sequence that is common and a second oligonucleotide probe that has a sequence that hybridizes only with the second sequence of the target polynucleotide. The kit further comprises one or more third oligonucleotide probes, each of the third oligonucleotide probes having a sequence that hybridizes only with a respective second sequence of one of the reference polynucleotide. The kit may also comprise reagents for conducting an isothermal amplification.

Another aspect of the present invention is a kit for use in an amplification and quantitation of a specific RNA. The kit comprises in packaged combination one or more reference RNA's, a promoter, an enzyme and a predetermined amounts of one or more reference polynucleotides. Each of the reference polynucleotides comprising a first sequence that is common with a first sequence of the target polynucleotide and a second sequence that is different from a second sequence of the target polynucleotide. The kit also comprises a predetermined amount of a first oligonucleotide probe that has a sequence that hybridizes with the sequence that is common. The first oligonucleotide probe is labeled with a sensitizer. A second oligonucleotide probe is included that has a sequence that hybridizes only with the second sequence of the target polynucleotide. The second oligonucleotide probe is labeled with a chemiluminescer. The kit further comprises one or more third oligonucleotide probes. Each of the third oligonucleotide probes has a sequence that hybridizes only with a respective second sequence of one of the reference polynucleotide. In addition, each of the third oligonucleotide probes is labeled with a chemiluminescer where the chemiluminescer is different from that of the second oligonucleotide probe and different for each of the third oligonucleotide probes.

DESCRIPTION OF THE SPECIFIC EMBODIMENTS

Figure 1:
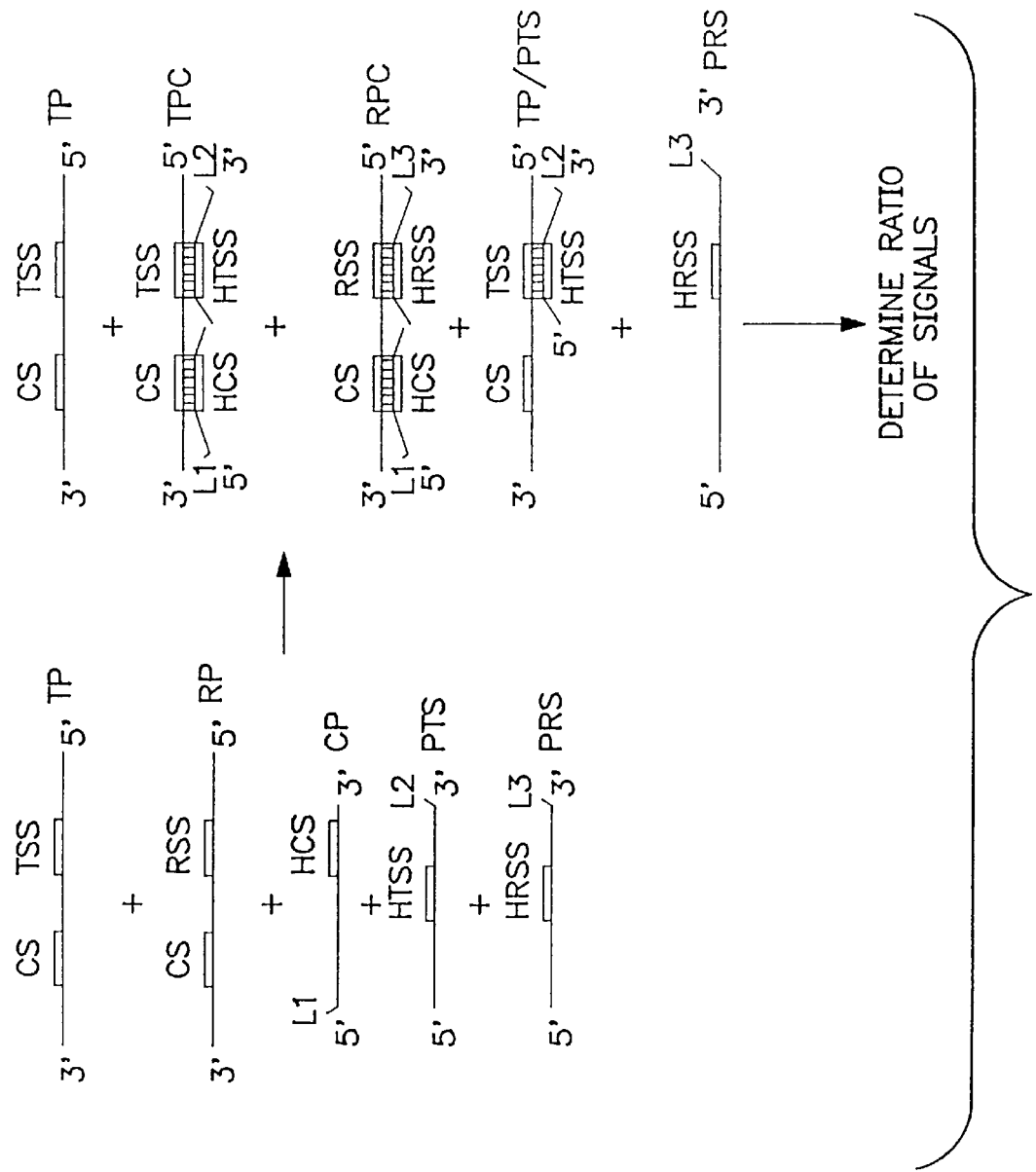
FIG. 1 is a schematic diagram depicting an embodiment in accordance with the present invention.

The present invention provides for detection of nucleic acid sequences, particularly, the products of nucleic acid amplification reactions. The invention is especially useful for monitoring the formation of a target nucleic acid produced during amplification under isothermal conditions such as that found in NASBA, 3SR, SDA or amplifications using Q-β-replicase. The method is dependent on the formation of the detectable complexes during the isothermal amplification process. A characteristic feature of the isothermal amplification process is the absence of a high temperature step of nucleic acid denaturation. This feature prevents dissociation of the detectable complexes of the single strand amplification product and the probes. The complexes that are formed simultaneously with the amplification process do not undergo dissociation thus avoiding the formation of single probe/product complexes, which would in turn lead to the prozone effect.

In the present invention the test nucleic acid sequence is amplified in the presence of a control sequence designed to be amplified as efficiently as the test sequence. The quantification of the specific amplification product is calculated as a ratio of signal obtained form the reference and test products. Two probes are used for the generation of signal from each of the products. The signal is generated by the association of the two probes, each carrying a reporter group, through hybridization to the single stranded amplification product. The signals from the test and reference products are distinct. The reference sequence is designed to differ from the test sequence by substituting a short sequence of the test with a unique sequence of similar size. This portion of the test and reference sequence is used for binding of the specific probes. The common probe is complementary to a sequence common for the two nucleic acid targets, the test and reference.

Binding of the oligonucleotide probes to the respective single stranded amplification products occurs simultaneously with the formation of the respective products. Limiting the amount of the common probe used results in a binding of the probe to a defined total amount of the single stranded amplification products, the sum of products of amplification of the test and reference targets. Thus, product formed in excess of the amount of the common probe is not considered in the quantitative analysis. In so far as the test and reference nucleic acid targets are amplified at equal efficiency, the amount of common probe binding to the two specific amplification products is dependent of the ratio of input of the two targets. Binding of the specific probes results in formation of detectable complexes that can be distinguished. An additional important feature of the disclosed method is limiting the quantification of the initial stages of the amplification process, which are expected to be more directly correlated with the initial amount of target than at later stages.

Before proceeding further with a description of the specific embodiments of the present invention, a number of terms will be defined.

Polynucleotide analyte—a compound or composition to be measured that is a polymeric nucleotide, which in the intact natural state can have about 30 to 5,000,000 or more nucleotides and in an isolated state can have about 20 to 50,000 or more nucleotides, usually about 100 to 20,000 nucleotides, more frequently 500 to 10,000 nucleotides. It is thus obvious that isolation of the analyte from the natural state often results in fragmentation. The polynucleotide analytes include nucleic acids, and fragments thereof, from any source in purified or unpurified form including DNA (dsDNA and ssDNA) and RNA, including t-RNA, m-RNA, r-RNA, mitochondrial DNA and RNA, chloroplast DNA and RNA, DNA-RNA hybrids, or mixtures thereof, genes, chromosomes, plasmids, the genomes of biological material such as microorganisms, e.g., bacteria, yeasts, viruses, viroids, molds, fungi, plants, animals, humans, and the like. The polynucleotide analyte can be only a minor fraction of a complex mixture such as a biological sample. The analyte can be obtained from various biological materials by procedures well known in the art. Some examples of such biological material by way of illustration and not limitation are disclosed in the following Table 1:

TABLE 1

| Microorganisms of interest include: | |
|---|---|
| Corynebacteria | |
| *Corynebacterium diphtheria* | |
| Pneumococci | |
| *Diplococcus pneumoniae* | |
| Streptococci | |
| *Streptococcus pyrogenes* | |
| *Streptococcus salivarus* | |
| Staphylococci | |
| *Staphylococcus aureus* | |
| *Staphylococcus albus* | |
| Neisseria | |
| *Neisseria meningitidis* | |
| *Neisseria gonorrhea* | |
| Enterobacteriaciae | |
| *Escherichia coli* | |
| *Aerobacter aerogenes* | The colliform |
| *Klebsiella pneumoniae* | bacteria |
| *Salmonella typhosa* | |
| *Salmonella choleraesuis* | The *Salmonellae* |
| *Salmonella typhimurium* | |
| *Shigella dysenteria* | |
| *Shigella schmitzii* | |
| *Shigella arabinotarda* | The *Shigellae* |
| *Shigella flexneri* | |
| *Shigella boydii* | |
| *Shigella sonnei* | |
| Other enteric bacilli | |
| *Proteus vulgaris* | |
| *Proteus mirabilis* | Proteus species |
| *Proteus morgani* | |
| *Pseudomonas aeruginosa* | |
| *Alcaligenes faecalis* | |
| *Vibrio cholerae* | |

TABLE 1-continued

Microorganisms of interest include:

| | |
|---|---|
| Hemophilus-Bordetella group | *Rhizopus oryzae* |
| *Hemophilus influenza, H. ducryi* | *Rhizopus arrhizua Phycomycetes* |
| *Hemophilus hemophilus* | *Rhizopus nigricans* |
| *Hemophilus aegypticus* | *Sporotrichum schenkii* |
| *Hemophilus parainfluenza* | *Flonsecaea pedrosoi* |
| *Bordetella pertussis* | *Fonsecacea compact* |
| Pasteurellae | *Fonsecacea dermatidis* |
| *Pasteurella pestis* | *Cladosporium carrionii* |
| *Pasteurella tulareusis* | *Phialophora verrucosa* |
| Brucellae | *Aspergillus nidulans* |
| *Brucella melitensis* | *Madurella mycetomi* |
| *Brucella abortus* | *Madurella grisea* |
| *Brucella suis* | *Allescheria boydii* |
| Aerobic Spore-forming Bacilli | *Phialophora jeanselmei* |
| *Bacillus anthracis* | *Microsporum gypseum* |
| *Bacillus subtilis* | *Trichophyton mentagrophytes* |
| *Bacillus megaterium* | *Keratinomyces ajelloi* |
| *Bacillus cereus* | *Microsporum canis* |
| Anaerobic Spore-forming Bacilli | *Trichophyton rubrum* |
| *Clostridium botulinum* | *Microsporum adouini* |
| *Clostridium tetani* | Viruses |
| *Clostridium perfringens* | Adenoviruses |
| *Clostridium novyi* | Herpes Viruses |
| *Clostridium septicum* | Herpes simplex |
| *Clostridium histolyticum* | Varicella (Chicken pox) |
| *Clostridium tertium* | Herpes Zoster (Shingles) |
| *Clostridium bifermentans* | Virus B |
| *Clostridium sporogenes* | Cytomegalovirus |
| MycobacteriaPox Viruses | |
| *Mycobacterium tuberculosis* Hominis | *Variola* (smallpox) |
| *Mycobacterium bovis* | *Vaccinia* |
| *Mycobacterium avium* | *Poxvirus bovis* |
| *Mycobacterium leprae* | *Paravaccinia* |
| *Mycobacterium paratuberculosis* | *Molluscum contagiosum* |
| Actinomycetes (fungus-like bacteria) | Picornaviruses |
| *Actinomyces lsaeli* | Poliovirus |
| *Actinomyces bovis* | Coxsackievirus |
| *Actinomyces naeslundii* | Echoviruses |
| *Nocardia asteroides* | Rhinoviruses |
| *Nocardia brasiliensis* | Myxoviruses |
| The Spirochetes | Influenza (A, B, and C) |
| *Treponema pallidum Spirillum minus* | Parainfluenza (1–4) |
| *Treponema pertenue Streptobacillus monoiliformis* | Mumps Virus |
| | Newcastle Disease Virus |
| *Treponema carateum* | Measles Virus |
| *Borrelia recurrentis* | Rinderpest Virus |
| *Leptospira icterohemorrhagiae* | Canine Distemper Virus |
| *Leptospira canicola* Respiratory | Syncytial Virus |
| Trypanasomes | Rubella Virus |
| Mycoplasmas | Arboviruses |
| *Mycoplasma pneumoniae* | |
| Other pathogens | Eastern Equine Eucephalitis Virus |
| *Listeria monocytogenes* | Western Equine Eucephalitis Virus |
| *Erysipelothrix rhusiopathiae* | Sindbis Virus |
| *Streptobacillus moniliformis* | Chikugunya Virus |
| *Donvania granulomatis* | Semliki Forest Virus |
| *Bartonella bacilliformis* | Mayora Virus |
| Rickettsiae (bacteria-like | St. Louis Encephalitis Virus |

TABLE 1-continued

Microorganisms of interest include:

parasites)

| | |
|---|---|
| *Rickettsia prowazekii* | California Encephalitis Virus |
| *Rickettsia mooseri* | Colorado Tick Fever Virus |
| *Rickettsia rickettsii* | Yellow Fever Virus |
| *Rickettsia conori* | Dengue Virus |
| *Rickettsia australis* | Reoviruses |
| *Rickettsia sibiricus* | Reovirus Types 1–3 |
| | Retroviruses |
| *Rickettsia akari* | Human Immunodeficiency Viruses (HIV) |
| *Rickettsia tsutsugamushi* | Human T-cell Lymphotrophic Virus I & II (HTLV) |
| *Rickettsia burnetti* | Hepatitis |
| *Rickettsia quintana* | Hepatitis A Virus |
| Chlamydia (unclassifiable parasites bacterial/viral) | Hepatitis B Virus |
| | Hepatitis nonA-nonB Virus |
| Chlamydia agents (naming uncertain) | Tumor Viruses |
| Fungi | Rauscher Leukemia Virus |
| *Cryptococcus neoformans* | Gross Virus |
| *Blastomyces dermatidis* | Maloney Leukemia Virus |
| *Hisoplasma capsulatum* | |
| *Coccidioides immitis* | Human Papilloma Virus |
| *Paracoccidioides brasiliensis* | |
| *Candida albicans* | |
| *Aspergillus fumigatus* | |
| *Mucor corymbifer* (*Absidia corymbifera*) | |

Also included are genes, such as hemoglobin gene for sickle-cell anemia, cystic fibrosis gene, oncogenes, cDNA, and the like.

The polynucleotide analyte, where appropriate, may be cleaved to obtain a fragment that contains a target polynucleotide sequence, for example, by shearing or by treatment with a restriction endonuclease or other site specific chemical cleavage method.

For purposes of this invention, the polynucleotide analyte, or a cleaved fragment obtained from the polynucleotide analyte, will usually be at least partially denatured or single stranded or treated to render it denatured or single stranded. Such treatments are well-known in the art and include, for instance, heat or alkali treatment. For example, double stranded DNA can be heated at 90–100° C. for a period of about 1 to 10 minutes to produce denatured material.

Amplification of nucleic acids or polynucleotides—any method that results in the formation of one or more copies of a nucleic acid or polynucleotide molecule or in the formation of one or more copies of the complement of a nucleic acid or polynucleotide molecule.

Exponential amplification of nucleic acids or polynucleotides—any method that depends on the product catalyzed formation of multiple copies of a nucleic acid or polynucleotide molecule or its complement. The amplification products are sometimes referred to as "amplicons." One such method for the enzymatic amplification of specific double stranded sequences of DNA is known as the polymerase chain reaction (PCR), as described above. This in vitro amplification procedure is based on repeated cycles of denaturation, oligonucleotide primer annealing, and primer extension by thermophilic template dependent polynucleotide polymerase, resulting in the exponential increase in copies of the desired sequence of the polynucleotide analyte flanked by the primers. The two different PCR primers, which anneal to opposite strands of the DNA, are positioned so that the polymerase catalyzed extension product of one primer can serve as a template strand for the other, leading to the accumulation of a discrete double stranded fragment whose length is defined by the distance between the 5' ends of the oligonucleotide primers.

Another method for amplification is mentioned above and involves amplification of a single stranded polynucleotide using a single oligonucleotide primer. The single stranded polynucleotide that is to be amplified contains two non-contiguous sequences that are complementary to one another and, thus, are capable of hybridizing together to form a stem-loop structure. This single stranded polynucleotide already may be part of a polynucleotide analyte or may be created as the result of the presence of a polynucleotide analyte.

Another method for achieving the result of an amplification of nucleic acids is known as the ligase chain reaction (LCR). This method uses a ligase enzyme to join pairs of preformed nucleic acid probes. The probes hybridize with each complementary strand of the nucleic acid analyte, if present, and ligase is employed to bind each pair of probes together resulting in two templates that can serve in the next cycle to reiterate the particular nucleic acid sequence.

Another method for achieving a nucleic acid amplification is the nucleic acid sequence based amplification (NASBA). This method is a promoter-directed, enzymatic process that induces in vitro continuous, homogeneous and isothermal amplification of a specific nucleic acid to provide RNA copies of the nucleic acid. The reagents for conducting NASBA include a first DNA primer with a 5' tail comprising a promoter, a second DNA primer, reverse transcriptase, RNAse-H, T7 RNA polymerase, NTP's and dNTP's.

Another method for amplifying a specific group of nucleic acids is the Q-beta-replicase method, which relies on the ability of Q-beta-replicase to amplify its RNA substrate exponentially. The reagents for conducting such an amplification include "midi-variant RNA" (amplifiable hybridization probe), NTP's, and Q-beta-replicase.

Another method for amplifying nucleic acids is known as 3SR and is similar to NASBA except that the RNAse-H activity is present in the reverse transcriptase. Amplification by 3SR is an RNA specific target method whereby RNA is amplified in an isothermal process combining promoter directed RNA polymerase, reverse transcriptase and RNase H with target RNA.

Another method for amplifying nucleic acids is the Transcription Mediated Amplification (TMA) used by Gen-Probe. The method is similar to NASBA in utilizing two enzymes in a self-sustained sequence replication. See Fahy, et al., patent application WO 91-US8488 911113.

Linear amplification of nucleic acids or polynucleotides—any method that depends on the self catalyzed formation of one or more copies of the complement of only one strand of a nucleic acid or polynucleotide molecule, usually a nucleic acid or polynucleotide analyte. Thus, the primary difference between linear amplification and exponential amplification is that the latter is autocatalyzed, that is, the product serves to catalyze the formation of more product, whereas in the former process the starting sequence catalyzes the formation of product but is not itself replicated. In linear amplification the amount of product formed increases as a linear function of time as opposed to exponential amplification where the amount of product formed is an exponential function of time.

Target polynucleotide—a sequence of nucleotides to be identified, usually existing within a portion or all of a polynucleotide analyte, the identity of which is known to an extent sufficient to allow preparation of various oligonucleotides, such as probes and primers, and other molecules necessary for conducting an amplification of the target polynucleotide.

In general, in primer extension amplification primers hybridize to, and are extended along (chain extended), at least the target sequence within the target polynucleotide and, thus, the target sequence acts as a template. The extended primers are chain "extension products." The target sequence usually lies between two defined sequences but need not. In general, the primers hybridize with the defined sequences or with at least a portion of such target polynucleotide, usually at least a ten-nucleotide segment at the 3'-end thereof and preferably at least 15, frequently 20 to 50 nucleotide segment thereof. The target sequence usually contains from about 30 to 5,000 or more nucleotides, preferably 50 to 1,000 nucleotides. The target polynucleotide is generally a fraction of a larger molecule or it may be substantially the entire molecule (polynucleotide analyte). The minimum number of nucleotides in the target polynucleotide sequence is selected to assure that the presence of target polynucleotide in a sample is a specific indicator of the presence of polynucleotide analyte in a sample. Very roughly, the sequence length is usually greater than about 1.6 log L nucleotides where L is the number of base pairs in the genome of the biologic source of the sample. The maximum number of nucleotides in the target polynucleotide is normally governed by the length of the polynucleotide analyte and its tendency to be broken by shearing, or other processes during isolation and any procedures required to prepare the sample for assay and the efficiency of detection and/or amplification of the sequence.

Oligonucleotide—a polynucleotide, usually single stranded, usually a synthetic polynucleotide but may be a naturally occurring polynucleotide. The oligonucleotide(s) are usually comprised of a sequence of at least 5 nucleotides, preferably, 10 to 100 nucleotides, more preferably, 20 to 50 nucleotides, and usually 10 to 30 nucleotides in length.

Various techniques can be employed for preparing an oligonucleotide utilized in the present invention. Such oligonucleotide can be obtained by biological synthesis or by chemical synthesis. For short sequences (up to about 100 nucleotides) chemical synthesis will frequently be more economical as compared to the biological synthesis. In addition to economy, chemical synthesis provides a convenient way of incorporating low molecular weight compounds and/or modified bases during the synthesis step. Furthermore, chemical synthesis is very flexible in the choice of length and region of the target polynucleotide binding sequence. The oligonucleotide can be synthesized by standard methods such as those used in commercial automated nucleic acid synthesizers. Chemical synthesis of DNA on a suitably modified glass or resin can result in DNA covalently attached to the surface. This may offer advantages in washing and sample handling. For longer sequences standard replication methods employed in molecular biology can be used such as the use of M13 for single stranded DNA as described by J. Messing (1983) *Methods Enzymol,* 101, 20–78.

Other methods of oligonucleotide synthesis include phosphotriester and phosphodiester methods (Narang, et al. (1979) *Meth. Enzymol* 68: 90) and synthesis on a support (Beaucage, et al. (1981) *Tetrahedron Letters* 22: 1859–1862) as well as phosphoramidate technique, Caruthers, M. H., et al., "Methods in Enzymology," Vol. 154, pp. 287–314 (1988), and others described in "Synthesis and Applications of DNA and RNA," S. A. Narang, editor, Academic Press, New York, 1987, and the references contained therein.

Oligonucleotide probe—an oligonucleotide employed in the present invention to bind to a portion of a polynucleotide such as an oligonucleotide probe or a target polynucleotide. The design and preparation of the oligonucleotide probes are important in performing the methods of this invention. A more detailed description of oligonucleotide probes in accordance with the present invention is found hereinbelow.

Oligonucleotide primer(s)—an oligonucleotide that is usually employed in a chain extension on a polynucleotide template such as in, for example, an amplification of a nucleic acid. The oligonucleotide primer is usually a synthetic nucleotide that is single stranded, containing a sequence at its 3'-end that is capable of hybridizing with a defined sequence of the target polynucleotide. Normally, an oligonucleotide primer has at least 80%, preferably 90%, more preferably 95%, most preferably 100%, complementarity to a defined sequence or primer binding site. The number of nucleotides in the hybridizable sequence of an oligonucleotide primer should be such that stringency conditions used to hybridize the oligonucleotide primer will prevent excessive random non-specific hybridization. Usually, the number of nucleotides in the oligonucleotide primer will be at least as great as the defined sequence of the target polynucleotide, namely, at least ten nucleotides, preferably at least 15 nucleotides and generally from about 10 to 200, preferably 20 to 50, nucleotides.

Nucleoside triphosphates—nucleosides having a 5'-triphosphate substituent. The nucleosides are pentose sugar derivatives of nitrogenous bases of either purine or pyrimidine derivation, covalently bonded to the 1'-carbon of the pentose sugar, which is usually a deoxyribose or a ribose. The purine bases include adenine(A), guanine (G), inosine (I), and derivatives and analogs thereof. The pyrimidine bases include cytosine (C), thymine (T), uracil (U), and derivatives and analogs thereof. Nucleoside triphosphates include deoxyribonucleoside triphosphates such as the four common triphosphates dATP, dCTP, dGTP and dTTP and ribonucleoside triphosphates such as the four common triphosphates rATP, rCTP, rGTP and rUTP.

The term "nucleoside triphosphates" also includes derivatives and analogs thereof, which are exemplified by those derivatives that are recognized in a similar manner to the underivatized nucleoside triphosphates. Examples of such derivatives or analogs, by way of illustration and not limitation, are those which are biotinylated, amine modified, alkylated, and the like and also include phosphorothioate, phosphite, ring atom modified derivatives, and the like.

Nucleotide—a base-sugar-phosphate combination that is the monomeric unit of nucleic acid polymers, i.e., DNA and RNA.

Modified nucleotide—is the unit in a nucleic acid polymer that results from the incorporation of a modified nucleoside triphosphate during an amplification reaction and therefore becoming part of the nucleic acid polymer.

Nucleoside—is a base-sugar combination or a nucleotide lacking a phosphate moiety.

Nucleotide polymerase—a catalyst, usually an enzyme, for forming an extension of a polynucleotide along a DNA or RNA template where the extension is complementary thereto. The nucleotide polymerase is a template dependent polynucleotide polymerase and utilizes nucleoside triphosphates as building blocks for extending the 3'-end of a polynucleotide to provide a sequence complementary with the polynucleotide template. Usually, the catalysts are enzymes, such as DNA polymerases, for example, prokaryotic DNA polymerase (I, II, or III), T4 DNA polymerase, T7 DNA polymerase, Klenow fragment, reverse transcriptase, Vent DNA polymerase, Pfu DNA polymerase, Taq DNA polymerase, and the like, derived from any source such as cells, bacteria, such as E. coli, plants, animals, virus, thermophilic bacteria, and so forth. RNA polymerases include T7 RNA polymerase, AMV polymerase, Q-beta-replicase, and so forth.

Wholly or partially sequentially—when the sample and various agents utilized in the present invention are combined other than concomitantly (simultaneously), one or more may be combined with one or more of the remaining agents to form a subcombination. Subcombination and remaining agents can then be combined and can be subjected to the present method.

Hybridization (hybridizing) and binding—in the context of nucleotide sequences these terms are used interchangeably herein. The ability of two nucleotide sequences to hybridize with each other is based on the degree of complementarity of the two nucleotide sequences, which in turn is based on the fraction of matched complementary nucleotide pairs. The more nucleotides in a given sequence that are complementary to another sequence, the more stringent the conditions can be for hybridization and the more specific will be the binding of the two sequences. Increased stringency is achieved by elevating the temperature, increasing the ratio of cosolvents, lowering the salt concentration, and the like.

Homologous or substantially identical polynucleotides—In general, two polynucleotide sequences that are identical or can each hybridize to the same polynucleotide sequence are homologous. The two sequences are homologous or substantially identical where the sequences each have at least 90%, preferably 100%, of the same or analogous base sequence where thymine (T) and uracil (U) are considered the same. Thus, the ribonucleotides A, U, C and G are taken as analogous to the deoxynucleotides dA, dT, dC, and dG, respectively. Homologous sequences can comprise DNA, RNA or modified polynucleotides and may be homoduplexes, e.g., RNA:RNA and DNA:DNA or heteroduplexes, e.g., RNA:DNA.

Complementary—Two sequences are complementary when the sequence of one can bind to the sequence of the other in an anti-parallel sense wherein the 3'-end of each sequence binds to the 5'-end of the other sequence and each A, T(U), G, and C of one sequence is then aligned with a T(U), A, C, and G, respectively, of the other sequence.

Non-contiguous—two sequences within a first single polynucleotide sequence are non-contiguous when the 5' end of one sequence is joined to the 3' end of the other sequence by more than a bond, usually by a chain of one or more nucleotides that are not hybridized to a second single polynucleotide strand to which the two sequences of the first single strand are hybridized to form a duplex.

Contiguous—two sequences within a first single polynucleotide strand are contiguous when the 5' end of one sequence is joined by a covalent bond directly to the 3' end of the other sequence without any intervening atoms or chain of nucleotides that are not hybridized to a second single polynucleotide strand to which the two sequences of the first single strand are hybridized to form a duplex.

Copy of a sequence—a sequence that was copied from, and has the same base sequence as, a single stranded polynucleotide sequence as differentiated from a sequence that is copied from and has a complementary base sequence to the sequence of such single stranded polynucleotide.

Means for extending a primer—a nucleotide polymerase or a single stranded template polynucleotide having a sequence other than at its 3'-end that can hybridize to at least the 3'-end of the primer or both. Means for extending a primer also includes nucleoside triphosphates or analogs thereof capable of acting as substrates for the enzyme and other materials and conditions required for enzyme activity such as a divalent metal ion (usually magnesium), pH, ionic strength, organic solvent (such as formamide), and the like.

Member of a specific binding pair ("sbp member")—one of two different molecules, having an area on the surface or in a cavity which specifically binds to and is thereby defined as complementary with a particular spatial and polar organization of the other molecule. The members of the specific binding pair are referred to as ligand and receptor (antiligand). These may be members of an immunological pair such as antigen-antibody, or may be operator-repressor, nuclease-nucleotide, biotin-avidin, hormones-hormone receptors, nucleic acid duplexes, IgG-protein A, DNA—DNA, DNA-RNA, and the like.

Ligand—any compound for which a receptor naturally exists or can be prepared.

Receptor ("antiligand")—any compound or composition capable of recognizing a particular spatial and polar organization of a molecule, e.g., epitopic or determinant site. Illustrative receptors include naturally occurring receptors, e.g., thyroxine binding globulin, antibodies, enzymes, Fab fragments, lectins, nucleic acids, repressors, protection enzymes, protein A, complement component C1q, DNA binding proteins or ligands and the like.

Small organic molecule—a compound of molecular weight less than 1500, preferably 100 to 1000, more preferably 300 to 600 such as biotin, fluorescein, rhodamine and other dyes, tetracycline and other protein binding molecules, and haptens, etc. The small organic molecule can provide a means for attachment of a nucleotide sequence to a label or to a support.

Support or surface—a porous or non-porous water insoluble material. The support can be hydrophilic or capable of being rendered hydrophilic and includes inorganic powders such as silica, magnesium sulfate, and alumina; natural polymeric materials, particularly cellulosic materials and materials derived from cellulose, such as fiber containing papers, e.g., filter paper, chromatographic paper, etc.; synthetic or modified naturally occurring polymers, such as nitrocellulose, cellulose acetate, poly (vinyl chloride), polyacrylamide, cross linked dextran, agarose, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Natural or synthetic assemblies such as liposomes, phospholipid vesicles, and cells can also be employed.

Binding of sbp members to a support or surface may be accomplished by well-known techniques, commonly available in the literature. See, for example, "Immobilized Enzymes," Ichiro Chibata, Halsted Press, New York (1978) and Cuatrecasas, *J. Biol. Chem.*, 245:3059 (1970). The surface can have any one of a number of shapes, such as strip, rod, particle, including bead, and the like.

Label—a member of a signal producing system. Usually the label is part of an oligonucleotide probe either being conjugated thereto or otherwise bound thereto or associated therewith and is capable of being detected directly or indirectly. The label may be part of the oligonucleotide primer. Labels include reporter molecules that can be detected directly by virtue of generating a signal, specific binding pair members that may be detected indirectly by subsequent binding to a cognate that contains a reporter molecule, oligonucleotide primers that can provide a template for amplification or ligation or a specific polynucleotide sequence or recognition sequence that can act as a ligand such as for a repressor protein, wherein in the latter two instances the oligonucleotide primer or repressor protein will have, or be capable of having, a reporter molecule. In general, any reporter molecule that is detectable can be used. The reporter molecule can be isotopic or nonisotopic, usually non-isotopic, and can be a catalyst, such as an enzyme, a polynucleotide coding for a catalyst, promoter, dye, fluorescent molecule, chemiluminescer, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, and the like. The reporter group can be a fluorescent group such as fluorescein, a chemiluminescent group such as luminol, a terbium chelator such as N-(hydroxyethyl) ethylenediaminetriacetic acid that is capable of detection by delayed fluorescence, and the like.

The label is a member of a signal producing system and can generate a detectable signal either alone or together with other members of the signal producing system. As mentioned above, a reporter molecule can be bound directly to a nucleotide sequence or can become bound thereto by being bound to an sbp member complementary to an sbp member that is bound to a nucleotide sequence. Examples of particular labels or reporter molecules and their detection can be found in U.S. patent application Ser. No. 07/555,323 filed Jul. 19, 1990, the relevant disclosure of which is incorporated herein by reference.

Signal Producing System—the signal producing system may have one or more components, at least one component being a label. The signal producing system generates a signal that relates to the presence or amount of target polynucleotide in a sample. The signal producing system includes all of the reagents required to produce a measurable signal. The labels and other reagents of the signal producing system must be stable at the temperatures used in an amplification of a target polynucleotide. Detection of the signal will depend upon the nature of the signal producing system utilized.

Preferably, the signal producing system is characterized in that the members of the system are chosen such that the binding of the second and third oligonucleotide probes to their respective duplexes to form termolecular complexes alters the signal generated by the signal producing system of the respective termolecular complexes. For example, in one approach the second oligonucleotide probe and the third oligonucleotide probe comprise a member of a different signal producing system and the signals are measured from the ternary complexes and a ratio of signals is determined. The first oligonucleotide probe may comprise a member of both signal producing systems. In another approach the first oligonucleotide probe in combination with each of the second oligonucleotide probe and the third oligonucleotide probe comprise members of different signal producing systems and the signals measured from the ternary complexes are used to determine a ratio of signals. In another approach the first oligonucleotide probe comprises a first member of a each of two signal producing systems and the second oligonucleotide probe and the third oligonucleotide probe each respectively comprise a second member of each of the signal producing systems. Preferably, when the first member is brought into close proximity with the second members of the signal producing system, a signal is produced.

A number of signal producing systems in accordance with the above may be employed. The following discussion is by way of illustration and not limitation. In one such system the first member is a catalyst such as an enzyme and the second members are catalysts such as enzymes that are different from the first enzyme and from each other and the products of the reaction of the enzyme comprising the first member are the substrates for the other of the enzymes. By employing different second enzymes signals are produced that can be differentiated and used to determine a ratio of signals that is related to concentration of the target polynucleotide.

A list of enzymes is found in U.S. Pat. No. 4,299,916 at column 30 to column 33. As mentioned above, of particular interest in the subject invention is the use of coupled catalysts, usually two or more enzymes, where the product of one enzyme serves as the substrate of the other enzyme. One of the enzymes is used as the label in the first oligonucleotide probe. Different second enzymes are used in the second and third oligonucleotide probes. The solute will be the substrate of any one of the enzymes, but preferably of an enzyme bound to the first oligonucleotide probe. The enzymatic reaction may involve modifying the solute to a product that is the substrate of another enzyme or production of compound that does not include a substantial portion of the solute, which serves as an enzyme substrate. The first situation may be illustrated by glucose-6-phosphate being catalytically hydrolyzed by alkaline phosphatase to glucose, wherein glucose is a substrate for glucose oxidase. The second situation may be illustrated by glucose being oxidized by glucose oxidase to provide hydrogen peroxide which would enzymatically react with the signal generator precursor to produce a signal generator. Coupled catalysts can also include an enzyme with a non-enzymatic catalyst. The enzyme can produce a reactant that undergoes a reaction catalyzed by the non-enzymatic catalyst or the non-enzymatic catalyst may produce a substrate (includes coenzymes) for the enzyme. For example, Medola blue can catalyze the conversion of NAD and hydroquinones to NADH, which reacts with FMN oxidoreductase and bacterial luciferase in the presence of long chain aldehydes to produce light. Examples of particular catalytic systems that may be utilized in the present invention are found in U.S. Pat. No. 4,299,916 at column 33, line 34, to column 38, line 32, the disclosure of which is incorporated herein by reference. For enzyme labels, additional members of the signal producing system include enzyme substrates and so forth. The product of the enzyme reaction is preferably a luminescent product or a fluorescent or non-fluorescent dye, any of which can be detected spectrophotometrically, or a product that can be detected by other spectrometric or electrometric means.

In another approach the first member of the signal producing system is a quencher and the second members are fluorescent compounds that emit at different wavelengths or with different decay rates. Fluorescers of interest generally emit light at a wavelength above 350 nm, usually above 400 nm and preferably above 450 nm. Desirably, the fluorescers have a high quantum efficiency, a large Stokes shift and are chemically stable under the conditions of their conjugation and use. The term fluorescer is intended to include substances that emit light upon activation and include fluorescent and phosphorescent substances, scintillators and chemiluminescent substances. In this approach the medium is irradiated with light and the fluorescence is determined. As will be appreciated, when the quencher is brought into close proximity to the fluorescent molecule by the formation of a termolecular complex, the fluorescence of the medium is decreased because of the absorption by the quencher of the light emitted by the fluorescer.

Fluorescers of interest fall into a variety of categories having certain primary functionalities. These primary functionalities include 1- and 2-aminonaphthalene, p,p'-diaminostilbenes, pyrenes, quaternary phenanthridine salts, 9-aminoacridines, imines, anthracenes, oxacarboxyamine, merocyanine, 3-aminoequilenin, perylene, bis-benzoxazole, bis-p-oxazolyl benzene, 1,2-benzophenazine, retinal, bis-3-aminopyridinium salts, hellebrigenin, tetracycline, sterophenol, benzimidazolylphenylamine, 2-oxo-3-chromen, indole, xanthene, 7-hydroxycoumarin, 4,5-benzimidazoles, phenoxazine, salicylate, strophanthidin, porphyrins, triarylmethanes, flavin and rare earth chelates oxides and salts. Exemplary fluorescers are enumerated in U.S. Pat. No. 4,318,707 at columns 7 and 8, the disclosure of which is incorporated herein by reference.

A diverse number of energy absorbers or quenchers may be employed. The quencher must be able to quench the fluorescence of the fluorescer when brought into proximity with the fluorescer by virtue of the binding of the probes. Quenchers are chromophores having substantial absorption higher than 310 nm, normally higher than 350 nm, and preferably higher than about 400 nm. Generally, the quencher is a fluorescent compound or fluorescer but energy acceptors that have weak or no fluorescence are also useful. For example, one group of quenchers is the xanthene dyes, which include the fluoresceins derived from 3,6-dihydroxy-o-phenyl-xanthhydrol and rhodamines, derived form 3,6-diamino-9-phenylxanthhydrol. Another group of compounds are the naphthylamines such as, e.g., 1-anilino-8-naphthalene sulfonate, 1-dimethylaminonaphthyl-5-sulfonate and the like. Other examples of quenchers that may be employed are those fluorescers of interest mentioned above wherein one fluorescer can absorb the energy of another fluorescer and quench its fluorescence.

Energy acceptors that are non-fluorescent can include any of a wide variety of azo dyes, cyanine dyes, 4,5-dimethoxyfluorescein, formazans, indophenols and the like.

Another example of quenchers is energy absorbent or quenching particles. Examples of such particles are carbon particles, such as charcoal, lampblack, graphite, colloidal carbon and the like. Besides carbon particles metal sols may also find use, particularly of the noble metals, gold, silver, and platinum. Other metal derived particles may include metal sulfides, such as lead, silver or copper sulfides or metal oxides, such as iron or copper oxide.

As mentioned above, Heller (U.S. Pat. No. 5,565,322) discloses donor and acceptor chromophores at column 9, line 37, to column 14, line 7, the disclosure of which is incorporated herein by reference. A further discussion of fluorescers and quenchers may also be found in U.S. Pat. Nos. 4,261,968, 4,174,384, 4,199,983 and 3,996,345, the relevant disclosures of which are incorporated herein by reference.

In another approach the first member of the signal producing system is a sensitizer and the second members are chemiluminescent compounds that emit at different wavelengths or with different decay rates. Alternatively, the first member is a chemiluminescent compound and the second members are sensitizers that can be independently excited by different wavelengths of light. Examples of chemiluminescent compounds and sensitizers are set forth in U.S. Ser. No. 07/923,069 filed Jul. 31, 1992, the disclosure of which is incorporated herein by reference. Particularly preferred are photosensitizers and photoactivatable chemiluminescent compounds such as described in U.S. Pat. No. 5,340,716 at column 19, line 30, to column 20, line 45, and column 22, line 58, to column 30, line 10, the disclosure of which is incorporated herein by reference. The sensitizers are those compounds that generate singlet oxygen usually by excitation with light. The sensitizer can be photoactivatable (e.g., dyes and aromatic compounds) or chemiactivated (e.g., enzymes and metal salts). Typical photosensitizers include acetone, benzophenone, 9-thioxanthone, eosin, 9,10-dibromoanthracene, methylene blue, metallo-porphyrins, such as hematoporphyrin, phthalocyanines, chlorophylls, rose bengal, buckminsterfullerene, etc., and derivatives thereof. Photoactivatable chemiluminescent compounds are substances that undergo a chemical reaction upon direct of sensitized excitation by light of upon reaction with singlet oxygen to form a metastable reaction product that is capable of decomposition with the simultaneous or subsequent emission of light, usually with the wavelength range of 250 to 1200 nm. Preferably, these compounds react with singlet oxygen to form dioxetanes or dioxetanones. The latter are usually electron rich olefins. Exemplary of such olefins are enol ethers, enamines, 9-alkylidene-N-alkylacridans, arylvinylethers, dioxenes, arylimidazoles, 9-alkylidene-xanthanes and lucigenin. Other compounds include luminol and other phthalhydrazides and chemiluminescent compounds that are protected form undergoing a reaction such as firefly luciferin, aquaphorin, luminol, etc.

Other components of the signal producing system may include substrates, enhancers, activators, chemiluminescent compounds, cofactors, inhibitors, scavengers, metal ions, specific binding substances required for binding of signal generating substances, and the like. Other components of the signal producing system may be coenzymes, substances that react with enzymic products, other enzymes and catalysts, and the like.

Termolecular complex—a complex formed in accordance with the present methods upon the binding of the two oligonucleotide probes with a target polynucleotide or a reference polynucleotide. Such complex is termolecular in that it involves three molecules, namely, the two oligonucleotide probes and the single strand of such target polynucleotide or reference polynucleotide. In the present invention the termolecular complex is relatively stable under the isothermal conditions employed.

Sample—any solution, synthetic or natural, containing a polynucleotide analyte or target polynucleotide including body fluids such as, for example, whole blood, blood fractions such as serum and plasma, synovial fluid, cerebrospinal fluid, amniotic fluid, semen, cervical mucus, sputum, saliva, gingival fluid, urine, and the like. The amount of the sample depends on the nature of the sample and the analyte contained therein. For fluid samples such as whole blood, saliva, urine and the like the amount of the sample is usually about 1 to 1000 nanoliters, more usually, about 10 to 100 nanoliters. The sample can be pretreated and can be prepared in any convenient medium, which does not interfere with the reactions conducted as part of the present methods.

Ancillary Materials—Various ancillary materials will frequently be employed in the methods carried out in accordance with the present invention. For example, buffers will normally be present in the assay medium, as well as stabilizers for the assay medium and the assay components. Frequently, in addition to these additives, proteins may be included, such as albumins, organic solvents such as formamide, quaternary ammonium salts, polycations such as dextran sulfate, surfactants, particularly non-ionic surfactants, binding enhancers, e.g., polyalkylene glycols, or the like.

In one embodiment the present invention is directed to a method for detecting the amount of a target polynucleotide in a sample. The target polynucleotide is single stranded either in the natural state or rendered single stranded as described above. A sample suspected of containing the target polynucleotide is combined in a medium with one or more of a reference polynucleotide and a predetermined amount of an oligonucleotide probe. The reference polynucleotide comprises a sequence that is common with a sequence of the target polynucleotide. The oligonucleotide probe has a sequence that hybridizes with the sequence that is common between the target polynucleotide and the reference polynucleotide. The combination is subjected to conditions for amplifying the target polynucleotide and the reference polynucleotide with substantially equal efficiency. The conditions permit formation of substantially non-dissociative complexes of the target polynucleotide and the reference polynucleotide, respectively, with the oligonucleotide probe. Furthermore, the predetermined amount of the oligonucleotide probe is less than the expected amount of the amplified target polynucleotide. The ratio of the amount of the complex of the target polynucleotide with the oligonucleotide probe to the amount of the complex of the reference polynucleotide with the oligonucleotide probe is determined. The ratio is related to the known amount of the reference polynucleotide to determine the amount of the target polynucleotide in the sample. Because the reference polynucleotide is amplified at substantially the same efficiency as the target polynucleotide and because the common oligonucleotide is employed in a predetermined amount less than the expected amount of the amplified target polynucleotide, the ratio of the amounts of the complexes at the end of amplification is directly related to the ratio of the amounts of the target and reference polynucleotides prior to amplification. Since the amount of the reference polynucleotide is known, the ratio of the complexes in conjunction with this known amount may be used to determine the amount of the target polynucleotide in the original sample.

The reference polynucleotide is specifically selected in light of the target polynucleotide. The reference polynucleotide may be naturally occurring or synthetic. As mentioned above, the reference polynucleotide has a sequence that is common with the target polynucleotide and a sequence that is different from that of the target polynucleotide. The common sequence is usually about 5 to about 100 nucleotides, preferably, about 10 to about 70 nucleotides, more preferably, about 20 to about 50 nucleotides, in length. It is preferred also that the common sequence of the reference polynucleotide be greater than about 90% homologous, preferably, greater than about 95% homologous, most preferably, fully homologous, to the common sequence of the target polynucleotide. A sequence that contains a greater number of G, C nucleotides has a stronger degree of binding to its complementary sequence and, thus, a greater G, C content in the common sequence lessens the need for full homology between the two common sequences.

The number of reference polynucleotides employed in the present method is determined by the range of quantification desired. In other words the greater the range, the more reference polynucleotides can be used.

As mentioned above, the reference polynucleotide should be amplified with substantially the same efficiency as the target polynucleotide. By the term "efficiency" is meant that the parameters of amplification such as rate of reaction and the like are substantially similar.

By the term "substantially the same efficiency" is meant that amplification of the reference polynucleotide proceed with efficiency that is about 90% similar to the amplification of the target polynucleotide, more preferably, about 95% similar to the efficiency of amplification of the target polynucleotide. In general, the efficiency of the amplification of the reference polynucleotide should be as close to that for the amplification of the target polynucleotide as possible so that an accurate determination of the amount of the target polynucleotide in a sample may be made. Most preferably, 100% similarity between the efficiencies of amplification of the target polynucleotide and the reference polynucleotide is desired.

The length and nucleotide content of the reference polynucleotide are chosen to achieve this efficiency. In general, the length of the reference polynucleotide should be within about 100 to about 1000 nucleotides of he sequence of the target polynucleotide to be amplified. Likewise, the nucleotide content of the amplification product of the reference polynucleotide should be within about at least 90% of the amplification product of the target polynucleotide. Other considerations are that the primers used for amplification of both target polynucleotide and reference oligonucleotide hybridize to the target polynucleotide with equal efficiency and that polymerase activity with both be substantially equally efficient.

The oligonucleotide probe has a sequence that is hybridizable with the common sequence. Usually, this sequence of the oligonucleotide probe is about 5 to about 100 nucleotides, preferably, about 10 to about 60 nucleotides, more preferably, about 20 to about 40 nucleotides, in length. The degree of complementarity of the sequence of the oligonucleotide probe and the common sequence of the target polynucleotide and the reference polynucleotide should be sufficient to achieve one of the objects of the present invention, namely, the ability to form complexes, respectively, with the target polynucleotide and the reference polynucleotide where the complexes are non-dissociative under the isothermal conditions. It is important that the complexes, once formed, not dissociate to any significant degree under the isothermal. By the term "not dissociate to any significant degree" is meant that the complex is stable to dissociation so that less than 1% of the oligonucleotide probe:target polynucleotide complex dissociates. Consequently, it is preferred that the sequence of the oligonucleotide probe be 70–100% complementary, preferably, 90–100% complementary, to the common sequence of the target polynucleotide and the reference polynucleotide. However, the degree of complementary depends on the relative lengths and nucleotide composition of the sequence of the oligonucleotide probes and the common sequences. It is preferred that the sequence of the oligonucleotide probe be greater than about 90% complementary, preferably, greater than about 95% complementary, most preferably, fully complementary, to the common sequence.

The sequence of the reference polynucleotide that is different from that in the target polynucleotide is usually about 10 to about 100 nucleotides, preferably, about 10 to about 50 nucleotides, more preferably, about 20 to about 40 nucleotides, in length. It is preferred also that the different sequence of the reference polynucleotide be greater than about 90% different, preferably, greater than about 95% different, most preferably, completely different, from the common sequence of the target polynucleotide.

In carrying out the present method, an aqueous medium is usually employed. In general, an aqueous medium is employed for the entire method in accordance with the present invention. Other polar cosolvents may also be employed, usually oxygenated organic solvents of from 1–6, more usually from 1–4, carbon atoms, including alcohols, ethers and the like. Usually these cosolvents, if used, are present in less than about 70 weight percent, more usually in less than about 30 weight percent.

The pH for the medium is usually in the range of about 4.5 to 9.5, more usually in the range of about 5.5 to 8.5, and preferably in the range of about 6 to 8. Various buffers may be used to achieve the desired pH and maintain the pH during the determination. Illustrative buffers include borate, phosphate, carbonate, Tris, barbital and the like. The particular buffer employed is not critical to this invention but in individual methods one buffer may be preferred over another. In general for amplification, the pH and temperature are chosen based on the particular method of amplification employed.

As mentioned above, the present method is conducted under isothermal conditions. In general, the temperature for the method is chosen so that the above complexes of the oligonucleotide probe with the target polynucleotide and reference polynucleotide, respectively, do not dissociate to any significant degree after formation. Thus, the temperature for the method is below the melting temperature of the above complexes. The particular temperature chosen depends on the salt concentration, pH, solvents used, the length of and composition of the common sequence and the sequence in the oligonucleotide probe and any other probes used in the method. For amplification by NASBA and 3SR, the reaction is usually conducted at isothermal temperature, which is usually about 38 to about 44° C., preferably about 41° C. For amplification by Q-beta replicase and SDA, the reaction is usually conducted at isothermal temperature, which is usually about 30 to about 45° C., preferably about 38° C.

The isothermal conditions include a uniform or constant temperature at which the present method is conducted. As mentioned above, the temperature for the method is chosen so that the above complexes of the oligonucleotide probe with the target polynucleotide and reference polynucleotide, respectively, do not dissociate to any significant degree after formation. By this is meant that the complexes do not dissociate more than about 5%, preferably no more than about 1%, most preferably, no more than about 0.1%. Although constant temperature is preferred, some fluctuation of the temperature may occur and still achieve the benefits of the present invention. Accordingly, the term "isothermal conditions" includes the use of a fluctuating temperature, particularly random or uncontrolled fluctuations in temperature. However, the fluctuation in temperature should not be more than about 5%, preferably no more than about 3%, most preferably, no more than about 1%. The fluctuation may be tolerated provided the temperature falls below, rather than above, the temperature of dissociation of the complexes formed in the present method. Generally, the particular isothermal temperature chosen is arrived at empirically by carrying out the present method at different temperatures and determining the optimum temperature resulting in the greatest amplification in accordance with the present invention. Computer models may also be used to select the appropriate temperature. A combination of the above may also be used. The temperature is generally determined by the amplification efficiency as determined by the method employed. This in turn is used to design the probes, since the melting temperature of the probe is a direct function of nucleotide content and length and can be calculated.

The amplification is conducted for a time sufficient so that all of the reference polynucleotide becomes part of a complex with the oligonucleotide probe. During this time period the target polynucleotide becomes complexed with free oligonucleotide probe, i.e., oligonucleotide probe not complexed with the reference polynucleotide. As mentioned above, the reference polynucleotide is employed in a predetermined amount. As a matter of convenience, it will usually be desirable to minimize the time period. The time period for amplification involving isothermal temperatures is usually about 10 to 90 minutes.

In the next step of the method, the ratio of the amount of the complex of the target polynucleotide with the oligonucleotide probe to the amount of the complex of the reference polynucleotide with the oligonucleotide probe is determined. To this end there must be some means for identifying the two complexes. In one approach a signal is produced by the complex of the target polynucleotide with the oligonucleotide probe. Such signal is different from a signal produced by the complex of the reference polynucleotide with the oligonucleotide probe. The ratio of the signals is related to the amount of the reference polynucleotide to determine the amount of the target polynucleotide in the sample. The signals produced may differ because a member of a signal producing system is used that recognizes only the complex of the oligonucleotide probe with the target polynucleotide and another member of a signal producing system is used that recognizes only the complex of the oligonucleotide probe with the reference polynucleotide. The corresponding complexes contain the other member of the respective signal producing system so that appropriate interactions between the respective members may occur to generate a signal. In another approach the respective complexes are identified and quantified directly.

In a preferred approach in accordance with the present invention, other probes are employed in addition to the oligonucleotide probe that has a sequence that hybridizes with the sequence that is common. In this embodiment a second oligonucleotide probe is employed that has a sequence that hybridizes only with a second sequence of the target polynucleotide. Also employed are one or more third oligonucleotide probes. Each of the third oligonucleotide probes has a sequence that hybridizes only with a respective second sequence of one of the reference polynucleotides.

The sequence of the second oligonucleotide probe that hybridizes only with a second sequence of the target polynucleotide is usually about 5 to about 80 nucleotides, preferably, about 10 to about 50 nucleotides, more preferably, about 15 to about 30 nucleotides, in length. The degree of complementarity of the sequence of the second oligonucleotide probe and the second sequence of the target polynucleotide should be sufficient to achieve one of the objects of the present invention, namely, the ability to form complexes, respectively, with the target polynucleotide and the reference polynucleotide where the complexes are substantially non-dissociative or do not dissociate to any substantial degree under the isothermal conditions employed in the method. Consequently, it is preferred that the sequence of the second oligonucleotide probe be 70–100% complementary, preferably, 90–100% complementary, to the second sequence of the target polynucleotide. However, as mentioned above, the degree of complementary depends on the relative lengths and nucleotide composition of the sequence of the oligonucleotide probes and the common sequences. It is preferred that the sequence of the second oligonucleotide probe be greater than about 90% complementary, preferably, greater than about 95% complementary, most preferably, fully complementary, to the second sequence of the target polynucleotide.

The second sequence of the target polynucleotide may be separated from the common sequence of the target polynucleotide by about 1 to about 20 nucleotides, usually, about 1 to about 10 nucleotides. In a preferred embodiment the second sequence and the common sequence of the target polynucleotide are contiguous.

The sequence of the third oligonucleotide probe that hybridizes only with a second sequence of the reference polynucleotide is 5 to about 80 nucleotides, preferably, about 10 to about 50 nucleotides, more preferably, about 15 to about 30 nucleotides, in length. The degree of complementarity of the sequence of the third oligonucleotide probe and the second sequence of the reference polynucleotide should be sufficient to achieve one of the objects of the present invention, namely, the ability to form complexes, respectively, with the target polynucleotide and the reference polynucleotide where the complexes are substantially non-dissociative or do not dissociate to any substantial degree under the isothermal conditions employed in the method. Consequently, it is preferred that the sequence of the third oligonucleotide probe be 70–100% complementary, preferably, 90–100% complementary, to the second sequence of the reference polynucleotide. However, as mentioned above, the degree of complementary depends on the relative lengths and nucleotide composition of the sequence of the oligonucleotide probes and the common sequences. It is preferred that the sequence of the third oligonucleotide probe be greater than about 90% complementary, preferably, greater than about 95% complementary, most preferably, fully complementary, to the second sequence of the reference polynucleotide.

The second sequence of the reference polynucleotide is separated from the common sequence of the reference polynucleotide by about 1 to about 20 nucleotides, usually, about 1 to about 10 nucleotides. In a preferred embodiment the second sequence and the common sequence of the target polynucleotide are contiguous. In a most preferred embodiment the number of nucleotides between the second sequence and the common sequence in the reference polynucleotide is the same as that in the target polynucleotide.

A different signal producing system is chosen for each of the respective second oligonucleotide probes and one or more third oligonucleotide probes corresponding to one or more of the reference polynucleotides. In this way the level of the different signals produced by the complexes formed are detected and a ratio is determined. The ratio of the respective signals is used to determine the ratio of the amount of the complex of the common (or first) oligonucleotide probe with the target polynucleotide to the amount of the complex of the common (or first) oligonucleotide probe with the reference oligonucleotide probe. To this end signal from the termolecular complex of the target polynucleotide and the first oligonucleotide probe and the second oligonucleotide probe is measured. Also measured are signals from the one or more termolecular complexes, each comprising a common (or first) oligonucleotide probe and a respective third oligonucleotide probe and its corresponding reference polynucleotide.

The ratio of the amount of the complex of the common (or first) oligonucleotide probe with the target polynucleotide to the amount of the complex of the common (or first) oligonucleotide probe with the reference oligonucleotide probe is then related to the known amount of the reference polynucleotide to determine the amount of the target polynucleotide in the sample. This is carried out for each of the reference polynucleotides employed.

The number of reference polynucleotides employed is dependent on a number of factors such as the desired range of quantification and the experimental accuracy of the determination of the differences between the target polynucleotide and the reference polynucleotide.

A third oligonucleotide probe is employed for each of the reference polynucleotides. Each of the third oligonucleotide probes has a sequence that hybridizes only with a respective second sequence of one of the reference polynucleotides.

An embodiment of the present method is depicted in FIG. 1 by way of illustration and not limitation. Target polynucleotide TP has a sequence CS that is common with sequence CS of reference polynucleotide RP. A common oligonucleotide probe CP has a sequence HCS that is hybridizable with sequence CS of TP and RP. Also included is second oligonucleotide probe PTS that comprises a sequence HTSS that is hybridizable with sequence TSS of TP. Also included is a third oligonucleotide probe PRS that has a sequence HRSS that is hybridizable with a sequence RSS in the RP. The above polynucleotides and oligonucleotide probes are combined in an appropriate medium and subjected to isothermal conditions. As the single stranded oligonucleotide amplification product is formed, complexes TRC and RPC are formed. As a result, substantially non-dissociative termolecular complexes TPC and RPC are formed. The reference polynucleotide RP and the first oligonucleotide probe CP are employed in predetermined amounts. Accordingly, the reaction medium contains unreacted second oligonucleotide probe PTS and unreacted third oligonucleotide probe PRS. Since the predetermined amount of the first oligonucleotide probe is less than the expected amount of amplified target polynucleotide, the reaction mixture also contains target polynucleotide that is hybridized only to the second oligonucleotide probe PTS. Depending on the amount of the amplified target polynucleotide formed and the amount of PTS, the reaction medium may also contain uncomplexed target polynucleotide or uncomplexed second oligonucleotide PTS. In the situation depicted in FIG. 1, an excess amount of amplified target polynucleotide is produced, so that the reaction medium contains uncomplexed target polynucleotide as well as target polynucleotide complexed with the second oligonucleotide probe (TP/PTS). The predetermined amount of the first oligonucleotide probe may be about 30 to 160-fold, preferably, about 50-fold, less than the expected amount of the amplified target polynucleotide.

After an appropriate incubation period for complex formation, signals are determined from the reaction medium. One signal results from the interaction of label L1 on CP and label L2 on PTS. The labels can be part of the common oligonucleotide probe and the second oligonucleotide probe initially. On the other hand, the labels can be included as separate reagents either in the initial reaction mixture or added subsequent to the incubation period. In the latter situation the common probe CP and the second oligonucleotide probe PTS may each respectively be capable of having the respective labels, L1 and L2. In this regard an sbp member may be attached to CP and the corresponding sbp member attached to label L1. The two sbp members bind to each other and L1 becomes part of the common probe CP. This situation is discussed above. The two sbp members may be, for example, hapten-antibody, nucleic acid-nucleic acid, and the like. Label L2 may be incorporated with the second oligonucleotide probe PTS in a similar manner. This is also true for label L3 and the third oligonucleotide probe RPS.

Labels L1 and L2 are part of a signal producing system as discussed above. When the complex TPC is formed, L1 and L2 can interact to produce a signal that is then measured. The signal produced by the interaction of L1 and L2 is different from the signal produced by the interaction of L1 and L3. This difference permits the determination of the ratio of the signals from complex TPC and RPC, which is then related to the amount of the target polynucleotide in the sample.

The amount of the target polynucleotide to be amplified can be as low as one or two molecules in a sample but generally may vary from about 10 to $10^{10}$, more usually from about $10^3$ to $10^8$ molecules in a sample preferably at least $10^{-21}$M in the sample and may be $10^{-10}$ to $10^{-19}$M, more usually $10^{-14}$ to $10^{-19}$M.

As mentioned above, the first oligonucleotide probe or common oligonucleotide probe is present in a predetermined amount. The predetermined amount of the first oligonucleotide probe is generally less than the expected amount of the amplified target polynucleotide. Usually, the amount is about 1%, more usually, about 0.1%, and preferably, about 0.01% less than that of the expected amount of the amplified target polynucleotide. The amount of the first oligonucleotide probe is usually about 5 to about 100 nM, more usually, about 10 to about 50 nM.

The concentrations of the second and third oligonucleotide probes will usually be similar, preferably identical, and may be an excess amount. Usually, the concentration of the second and third oligonucleotide probes is consistent with the concentration of the other reagents in the reaction. For example, the concentration may be about 5 to about 100 M, more usually, about 10 to about 50 M.

As mentioned above, the reference polynucleotide (or reference polynucleotides) is present in a predetermined amount so that the ratio of the signals determined may be related to the predetermined amount of the reference polynucleotide to determine the amount of target polynucleotide that was originally in the sample. The predetermined amount of the reference polynucleotide is usually about 10 to about $10^6$, more usually, $10^2$ to about $10^5$, molecules per assay.

The concentration of an enzyme that may be used in an amplification is usually determined empirically. Preferably, a concentration is used that is sufficient such that further increase in the concentration does not decrease the time for the amplification by over 5-fold, preferably 2-fold. The primary limiting factor generally is the cost of the reagent.

For amplification under isothermal conditions that may involve primer extension, the amount of the oligonucleotide primer(s) will be at least as great as the number of copies desired and will usually be $10^{-13}$ to $10^{-8}$ moles per sample, where the sample is 1–1,000 µL. Usually, the primer(s) are present in at least $10^{-9}$ M, preferably $10^{-7}$ M, and more preferably at least about $10^{-6}$ M. Preferably, the concentration of the oligonucleotide primer(s) is substantially in excess over, preferably at least 100 times greater than, more preferably, at least 1000 times greater than, the concentration of the target polynucleotide sequence.

For amplifications involving primer extension, the concentration of the nucleoside triphosphates in the medium can vary widely; preferably, these reagents are present in an excess amount. The nucleoside triphosphates are usually present in $10^{-6}$ to $10^{-2}$M, preferably $10^{-5}$ to $10^{-3}$M.

As mentioned above one aspect of the present invention provides for quantitation of a target polynucleotide in a sample suspected of containing the target polynucleotide. The present invention has particular application to amplification reactions conducted at isothermal temperature. All of the necessary reagents for amplification and detection can be included in the reaction mixture prior to amplification and it is not necessary to open the reaction vessel after amplification and prior to detection. Thus, contamination is avoided. At the very least, complexes containing labels and any remaining members of the signal producing system can be added after amplification but without a separation step prior to detection. In some amplification procedures a preincubation may be desirable for the purpose of denaturation of double stranded structure and secondary intra strand structure. This preincubation is usually carried out at a temperature of about 50° C. to about 90° C., preferably, about 60° C. to about 70° C., for a period of about 1 to about 30 minutes, preferably, about 5 to about 10 minutes. In this regard all of the reagents may be combined except for the enzyme necessary for a particular amplification. Once the preincubation is carried out, the enzyme is added and the amplification is allowed to proceed.

It should be noted that the length of the various oligonucleotide probes and the relevant sequences contained therein may be greater or less than that indicated above. The length depends on a number of factors such as the possibility of strand invasion, whether the nucleotides are natural or modified, the temperature, the pH, the salt concentration of the medium, and so forth. In general, the length of the above sequences should be sufficient to ensure substantially non-dissociative complexes following hybridization to the amplification product at the amplification conditions of temperature, buffer and oligonucleotide probe concentration.

Detection of the signal, and the conditions therefor, depend upon the nature of the signal producing system utilized. Such conditions are well known in the art. If the reporter molecule is an enzyme, additional members of the signal producing system would include enzyme substrates and so forth. The product of the enzyme reaction is preferably a luminescent product, or a fluorescent or non-fluorescent dye, any of which can be detected spectrophotometrically, or a product that can be detected by other spectrometric or electrometric means. If the reporter molecule is a fluorescent molecule, the medium can be irradiated and the fluorescence determined. Where the label is a radioactive group, the first probe can be separated from the duplex of the first and second probes and one of the fractions can be counted to determine the radioactive count.

The association of the labels within the termolecular complex may also be determined by using labels that provide a signal only if the labels become part of, or dissociate from, the complex. The binding of the single stranded target polynucleotide, if present, to the second probe causes displacement of the first probe from the second probe and thereby alters a signal generated by the signal producing system. This approach is particularly attractive when it is desired to conduct the present invention in a homogeneous manner. Such systems include enzyme channeling immunoassay, fluorescence energy transfer immunoassay, electrochemiluminescence assay, induced luminescence assay, latex agglutination and the like.

In one aspect of the present invention detection of the complex is accomplished by employing at least one suspendable particle as a support, which may be bound directly to a nucleic acid strand or may be bound to an sbp member that is complementary to an sbp member attached to a nucleic acid strand, either first or second oligonucleotide probe. Such a particle serves as a means of segregating the bound target polynucleotide sequence from the bulk solution. A second label, which is attached to the other of the first or second oligonucleotide probes, becomes part of the termolecular complex. Typical labels that may be used in this particular embodiment are fluorescent labels, particles containing a sensitizer and a chemiluminescent olefin (see U.S. Ser. No. 07/923,069 filed Jul. 31, 1992, the disclosure of which is incorporated herein by reference), chemiluminescent and electroluminescent labels.

Preferably, the particle itself can serve as part of a signal producing system that can function without separation or segregation. The second label is also part of the signal producing system and can produce a signal in concert with the particle to provide a homogeneous assay detection method. A variety of combinations of labels can be used for this purpose. When all the reagents are added at the beginning of the reaction, the labels are limited to those that are stable to the temperatures used for amplification.

The particles, for example, may be simple latex particles or may be particles comprising a sensitizer, chemiluminescer, fluorescer, dye, and the like. Typical particle/reporter molecule pairs include a dye crystallite and a fluorescent label where binding causes fluorescence quenching or a tritiated reporter molecule and a particle containing a scintillator. Typical reporter molecule pairs include a fluorescent energy donor and a fluorescent acceptor dye. Typical particle pairs include (1) two latex particles, the association of which is detected by light scattering or turbidimetry, (2) one particle capable of absorbing light and a second label particle which fluoresces upon accepting energy from the first, and (3) one particle incorporating a sensitizer and a second particle incorporating a chemiluminescer as described for the induced luminescence immunoassay referred to in U.S. Ser. No. 07/704,569, filed May 22, 1991, entitled "Assay Method Utilizing Induced Luminescence", which disclosure is incorporated herein by reference.

Briefly, detection of the termolecular complex using the induced luminescence assay as applied in the present invention involves employing a photosensitizer as part of one label and a chemiluminescent compound as part of the other label. If the complex is present the photosensitizer and the chemiluminescent compound come into close proximity. The photosensitizer generates singlet oxygen and activates the chemiluminescent compound when the two labels are in close proximity. The activated chemiluminescent compound subsequently produces light. The amount of light produced is related to the amount of the complex formed.

If the amplification uses a DNA polymerase, preferably, the oligonucleotide probes are blocked at the 3'-end to avoid any potential interference with and during amplification. Blocking may be accomplished, for example, by employing a group that cannot undergo chain extension, such as, for example, an unnatural group such as a 3'-phosphate, a 3'-terminal dideoxy, an a basic ribophosphate, a polymer or surface, or other means for inhibiting chain extension. Alternatively, a polynucleotide that does not hybridize to the amplicon is attached to the 3'-end. Such an end group can be introduced at the 3' end during solid phase synthesis or a group can be introduced that can subsequently be modified. For example, in order to introduce dextran at the 3'-end a ribonucleotide can be introduced at the 3'-end and then oxidized with periodate followed by reductive amination of the resulting dialdehyde with borohydride and aminodextran. The details for carrying out the above modifications are well known in the art and will not be repeated here.

Figure 2:
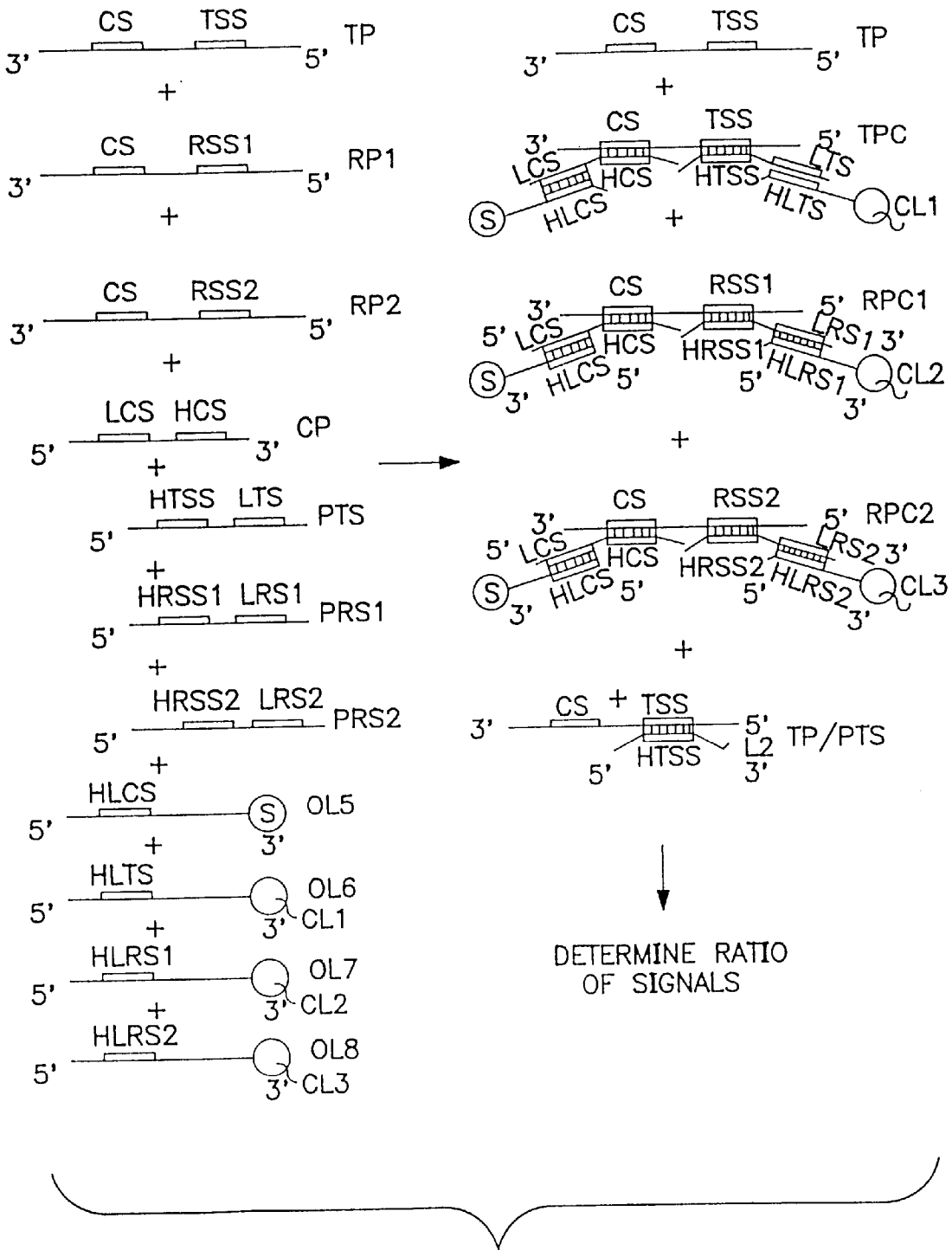
FIG. 2 is a schematic diagram depicting an alternate embodiment in accordance with the present invention.

An embodiment of the above is depicted in FIG. 2 by way of illustration and not limitation. Target polynucleotide TP has a sequence CS that is common with sequence CS of reference polynucleotide RP1 and reference polynucleotide RP2. In addition to the common sequence, RP1 has a sequence RSS1 that is different from sequence TSS of the target polynucleotide. In addition to the common sequence, RP2 has a sequence RSS2 that is different from sequence TSS of the target polynucleotide and from the sequence RSS1 of RP1. A common oligonucleotide probe CP has a sequence HCS that is hybridizable with sequence CS of TP and RP1 and RP2. CP also comprises sequence LCS, which is part of one of the signal producing systems employed in the method depicted in FIG. 2. LCS is hybridizable with sequence HLCS in oligonucleotide OL5, which also comprises a bead having a sensitizer S associated therewith. Also included is second oligonucleotide probe PTS that comprises a sequence HTSS that is hybridizable with sequence TSS of TP. PTS also comprises a sequence LTS that is part of one of the signal producing systems employed in the method depicted in FIG. 2. LTS is hybridizable with sequence HLTS in oligonucleotide OL6, which also comprises a bead having a chemiluminescer, CL1, associated therewith. Also included is a third oligonucleotide probe PRS1 that has a sequence HRSS1 that is hybridizable with a sequence RSS1 in the RP1. PRS1 also comprises sequence LRS1, which is part of another of the signal producing systems employed in the method depicted in FIG. 2. LRS1 is hybridizable with sequence HLRS1 in oligonucleotide OL7, which also comprises a bead having a chemiluminescer, CL2, associated therewith. Also included is a fourth oligonucleotide probe PRS2 that has a sequence HRSS2 that is hybridizable with a sequence RSS2 in the RP2. PRS2 also comprises sequence LRS2, which is part of another of the signal producing systems employed in the method depicted in FIG. 2. LRS2 is hybridizable with sequence HLRS2 in oligonucleotide OL8, which also comprises a bead having a chemiluminescer, CL3, associated therewith.

The above polynucleotides and oligonucleotide probes are combined in an appropriate medium and subjected to isothermal conditions. As a result, substantially non-dissociative termolecular complexes TPC, RPC1 and RPC2 are formed. Complex TPC includes OL5 and OL6, by virtue of the presence of sequences that are hybridizable to sequences in the respective oligonucleotide probes CP and PTS. Complex RPC1 includes OL5 and OL7, by virtue of the presence of sequences that are hybridizable to sequences in the respective oligonucleotide probes CP and PRS1. Complex RPC2 includes OL5 and OL8, by virtue of the presence of sequences that are hybridizable to sequences in the respective oligonucleotide probes CP and PRS2.

As mentioned above, sensitizer S forms part of each of three signal producing systems corresponding, respectively, to chemiluminescers CL1, CL2 and CL3. As a result of the formation of the termolecular complexes TPC, RPC1 and RPC2, the sensitizer is brought into close proximity with CL1, CL2 and CL3, respectively. The chemiluminescers differ by virtue of emitting light of different wavelength, thus permitting discrimination of signals produced by the respective termolecular complexes.

The reference polynucleotides RP1 and RP2 and the first oligonucleotide probe CP are employed in predetermined amounts. Accordingly, the reaction medium contains unreacted second oligonucleotide probe PTS and unreacted third and fourth oligonucleotide probes, PRS1 and PRS2, respectively. Since the predetermined amount of the first oligonucleotide probe CP is less than the expected amount of amplified target polynucleotide, the reaction mixture also contains target polynucleotide that is hybridized only to the second oligonucleotide probe PTS. Depending on the amount of the amplified target polynucleotide formed and the amount of PTS, the reaction medium may also contain uncomplexed target polynucleotide or uncomplexed second oligonucleotide PTS as well as excess amounts of OL5, OL6, OL7 and OL8. In the situation depicted in FIG. 2, an excess amount of amplified target polynucleotide is produced, so that the reaction medium contains uncomplexed target polynucleotide as well as target polynucleotide complexed with the second oligonucleotide probe (TP/PTS).

After an appropriate incubation period for complex formation, signals are determined from the reaction medium. The difference is signals from the respective termolecular complexes permits the determination of the ratio of the signals from complex TPC and RPC1 and RPC2, which is then related to the amount of the target polynucleotide in the sample.

The present method may also be used to monitor the progress of an amplification conducted under isothermal conditions. A signal is measured at the outset of the amplification. For example, the signal may be produced as a result of the induced luminescence resulting from the interaction of the sensitizer with oxygen to form singlet oxygen, which reacts with the chemiluminescent compound to produce a product that spontaneously produces luminescence. The level of signal is measured periodically during the amplification. During the amplification the signal measured initially is changed as a result of the increase in concentration of the complex of the target polynucleotide with the first oligonucleotide probe and the second oligonucleotide probe. Since more sensitizer is in close proximity of the chemiluminescent compound, signal increases. This increase in signal can be monitored as an indication of the progress of the amplification of the target polynucleotide. When the increase in signal is no longer observed, the amplification is complete.

As mentioned above, the nature of the signal from each of the reference polynucleotides and that for the target polynucleotide must be separately detectable. This entails different signal producing system members for each of the above. For example, in the example depicted in FIG. 2, each of the respective chemiluminescent particles corresponding to the different reference polynucleotides and the target polynucleotide may emit at different wavelengths of light as a result of the sensitization by the sensitizer.

As mentioned above, a particular advantage of the present invention is that excess target polynucleotide does not interfere with the determination. This results from the fact that the first oligonucleotide probe is present in an amount that is less than the expected amount of amplified target polynucleotide.

Another particular example of the present method as applied to the detection of an RNA target polynucleotide in a sample suspected of containing the target polynucleotide is next described by way of illustration and not limitation. The amplification method chosen is NASBA. Accordingly, a measured amount of the sample suspected of containing the RNA target polynucleotide is combined with a predetermined amount of reference polynucleotides H and J. The predetermined amount of H is 100 copies and the predetermined amount of J is 1000 copies. The RNA is isolated from the sample and combined in a reaction medium with all of the reagents for conducting a NASBA amplification, namely, RNA polymerase, a DNA primer with a promoter sequence, a second DNA primer, T7 polymerase reverse transcriptase, RNAse-H, nucleotide triphosphates and deoxynucleoside triphosphates. These reagents are provided in amounts to achieve a concentration of the RNA target polynucleotide, if present, in the reaction medium after NASBA amplification of about $10^{-7}$ to $10^{-5}$ M. The reaction medium further contains a first oligonucleotide probe K, which is a universal probe and has the energy donor 7-dimethylaminocoumarin-3-carboxylic acid attached to a terminal nucleotide thereof at the 5' end. The medium also includes a second oligonucleotide probe K that has a sequence complementary to a sequence in the target polynucleotide, a third oligonucleotide probe L that has a sequence complementary to a sequence in reference polynucleotide M, and a fourth oligonucleotide probe N that has a sequence complementary to a sequence in reference polynucleotide H. Universal probe K has a sequence that is complementary to a sequence in the target polynucleotide as well as oligonucleotides L, M and N. Oligonucleotide probe L has fluorescein attached to a terminal nucleotide at the 3' end thereof, oligonucleotide probe M has the fluorophore, phycoerythrin, attached to a terminal nucleotide at the 3' end thereof and oligonucleotide N has phycoerythrin conjugated to allophycocyanine attached to a terminal nucleotide at the 3' end thereof. The reaction medium is subjected to conditions for carrying out the NASBA amplification, namely, a temperature of 41° C. for a time of 90 minutes.

As indicated above, the detection and quantitation of the target polynucleotide can be carried out at the end of the amplification or during the amplification. In the latter situation, the amplification is conducted and a determination of the signal is determined at a variety of points in time. This is achieved by irradiating the reaction medium at a wavelength of 415 nm and determining the ratios of the light emitted at three different wavelengths corresponding to the emission maxima of the three fluorophors fluorescein 520 nm, phycoerythrin 576 nm and phycoerythrin/allophycocyanine 660 nm. The target polynucleotide, if present, hybridizes with K and with L to give a termolecular complex TKL. Likewise, reference polynucleotide H hybridizes with K and M to give termolecular complex HKM, and reference polynucleotide J hybridizes with K and N to give termolecular complex JKN.

Briefly, detection using the induced luminescence assay as applied in the present invention involves an energy donor as part of one label and a fluorescent energy acceptor as part of the other label in a particular signal producing system. If the target polynucleotide is present the donor and the acceptor come into close proximity and the fluorescent acceptor is activated and emits light in relation to the amount of the complex formed.

As a matter of convenience, predetermined amounts of reagents employed in the present invention can be provided in a kit in packaged combination. The kit comprises in packaged combination one or more reagents for conducting an amplification and detection of the amplified product as well as the oligonucleotide probes and the reference polynucleotides. An example of a kit in accordance with the present invention is a kit comprising reagents for conducting an amplification of the target polynucleotide together with one or more reference polynucleotides, first and second oligonucleotide probes and one or more third oligonucleotide probes. Each reference polynucleotide is present in a known predetermined amount and each comprises a sequence that is common with a sequence of the target polynucleotide. The first oligonucleotide probe is employed in a predetermined amount and hybridizes with the sequence that is common between the target and the reference polynucleotides. The second oligonucleotide probe has a sequence that hybridizes only with the second sequence of the target polynucleotide. The third oligonucleotide probe has a sequence that hybridizes only with a respective second sequence of the reference polynucleotide.

Another example of a kit in accordance with the present invention is a kit for RNA amplification. Such a kit comprises reference RNA's, a promoter, an enzyme, one or more reference polynucleotides, first and second oligonucleotide probes and one or more third oligonucleotide probes, each corresponding to a reference polynucleotide. One of the first and second oligonucleotide probes is labeled with a sensitizer and the other thereof is labeled with a chemiluminescer. One of the first and third oligonucleotide probes is labeled with a sensitizer and the other thereof is labeled with a chemiluminescer. Usually, the first oligonucleotide probe is labeled with a sensitizer and the second and third oligonucleotide probes are labeled with a different chemiluminescer. In this way the signals from the respective labels are differentially detectable.

The kit can further include any additional members of a signal producing system and also various buffered media, some of which may contain one or more of the above reagents. The kits above can further include in the packaged combination reagents for conducting an amplification of the target polynucleotide. For example, in the case of NASBA, the kit may include a first DNA primer with a 5' tail comprising a promoter, a second DNA primer, reverse transcriptase, RNAse-H, T7 RNA polymerase, NTP's and dNTP's.

The relative amounts of the various reagents in the kits can be varied widely to provide for concentrations of the reagents necessary to achieve the objects of the present invention. Under appropriate circumstances one or more of the reagents in the kit can be provided as a dry powder, usually lyophilized, including excipients, which on dissolution will provide for a reagent solution having the appropriate concentrations for performing a method or assay in accordance with the present invention. Each reagent can be packaged in separate containers or some reagents can be combined in one container where cross-reactivity and shelf life permit. The kits may also include a written description of a method in accordance with the present invention as described above.

EXAMPLES

The invention is demonstrated further by the following illustrative examples. Parts and percentages recited herein are by weight unless otherwise specified. Temperatures are in degrees centigrade (° C.).

Melting points were determined on a Hoover capillary apparatus and are uncorrected. 'HNMR spectra were recorded on a Brucker WP-250 MHz or Brucker WP-300 MHz NMR spectrometer. Chemical shifts were reported in parts per million ($\delta$ 0.0). NMR multiplicities are recorded by use of the following abbreviations: s, singlet; d, doublet; t, triplet; m, multiplet; Hz, hertz. Infrared spectra were recorded on a Perkin-Elmer 297IR spectrometer. Desorption chemical ionization (C.I.) and electron ionization (E.I.) were done on a Varian-MAT 311A, double focusing high-resolution mass spectrometer. A Finnigan TSQ-70 or MAT-8230 was used for fast atom bombardment mass spectra (FAB/LSIMS). UV-visible absorption spectra were done on a HP 8452A diode array spectrophotometer. Fluorescence and chemiluminescence measurements were done on a Spex fluorolog spectrophotometer or a Perkin Elmer 650-40 spectrophotometer. Chemiluminescence measurements were also performed on an in-house chemiluminometer (Oriel box).

Toluene was distilled from sodium over argon. Unless mentioned otherwise, all solvents were used without purification, and most reactions were carried out under argon. Silica gel used for flash chromatography was 230–400mesh ASTM, purchased from Scientific Products while preparative plates (1000$\mu$) and analytical plates were purchased from Analtech.

C-28 thioxene, substituted N-phenyl oxazine and thioxene attached to 9,10-bis(phenylethynyl) anthracene (BPEA) were prepared as described below. 2-Chloro 9,10-bis (phenylethynyl) anthracene (1-CI-BPEA) and rubrene (5,6, 11,12-tetraphenyl naphthacene) were purchased from Aldrich Chemical Co. Rubrene was recrystallized from methylene chloride and stored at 4° C. in a brown bottle prior to use. Silicon phthalocyanine was prepared as described below and phthalocyanine tetrasulfonates was obtained from Ultra Diagnostics, Inc. Carboxylate-modified polystyrene (latex) particles were purchased from Seradyn, Inc. The particles were 203±4.0 nM. The carboxyl parking area was 49.5 angstroms squared (0.09 milliequivalents/g). Solids were 10% (100 mg/ml).

2-ethoxyethanol was from Aldrich Chemical Co. and was redistilled under vacuum. Sodium hydroxide was 0.1 N. Isopropanol was from Aldrich Chemical Co.

Unless otherwise indicated, oligonucleotides used in the following examples were prepared by synthesis using an automated synthesizer and were purified by gel electrophoresis or HPLC.

The following abbreviations have the meanings set forth below:

Tris HCl—Tris(hydroxymethyl)aminomethane-HCl (a 10×solution) from BioWhittaker, Walkersville, Md.

DTT—dithiothreitol from Sigma Chemical Company, St. Louis, Mo.

HPLC—high performance liquid chromatography.
DPP—4,7-diphenylphenanthroline from Aldrich Chemical Company, Milwaukee Wis.
BSA—bovine serum albumin from Sigma Chemical Company, St. Louis Mo.
ELISA—enzyme linked immunosorbent assay as described in "Enzyme-Immunoassay," Edward T. Maggio, CRC Press, Inc., Boca Raton, Fla. (1980)
bp—base pairs
ddc—dideoxycytidine
g—grams
mmol—millimolar
DMF—dimethyl formamide
THF—tetrahydrofuran
LSIMS—fast ion bombardment mass spectroscopy
NMR—nuclear magnetic resonance spectroscopy
TMSCI—tetramethylsilylchloride
EDAC—1-ethyl-3-(3-dimethylaminopropyl)-carbodiimide hydrochloride.
MES—2-(N-morpholino)ethane sulfonic acid.
SPDP—N-succinimidyl 3-(2-pyridylthio)-propionate.
Sulfo-SMCC—N-sulfosuccinimidyl-4-(N-maleimidomethyl)cyclohexane-1-carboxylate.
TCEP—tris-carboxyethyl phosphine.
Preparation of Reagents
C-28 Thioxene:
To a solution of 4-bromoaniline (30 g, 174 mmol) in dry DMF (200 mL) was added 1-bromotetradecane (89.3 mL, 366 mmol) and N,N-diisopropylethylamine (62.2 mL, 357 mmol). The reaction solution was heated at 90° C. for 16 hr under argon before being cooled to room temperature. To this reaction solution was again added 1-bromotetradecane (45 mL, 184 mmol) and N,N-diisopropylethylamine (31 mL, 178 mmol) and the reaction mixture was heated at 90° C. for another 15 hr. After cooling, the reaction solution was concentrated in vacuo and the residue was diluted with $CH_2Cl_2$ (400 mL). The $CH_2Cl_2$ solution was washed with 1 N aqueous NaOH (2×), $H_2O$, and brine, was dried over $Na_2SO_4$ and was concentrated in vacuo to yield a dark brown oil (about 110 g). Preparative column chromatography on silica gel by a Waters 500 Prep LC system eluting with hexane afforded a yellow oil that contained mainly the product (4-bromo-N,N-di-($C_{14}H_{29}$)-aniline) along with a minor component 1-bromotetradecane. The latter compound was removed from the mixture by vacuum distillation (bp 105–110° C., 0.6 mm) to leave 50.2 g (51%) of the product as a brown oil. To a mixture of magnesium turnings (9.60 g, 395 mmol) in dry THF (30 mL) under argon was added dropwise a solution of the above substituted aniline product (44.7 g, 79 mmol) in THF (250 mL). A few crystals of iodine were added to initiate the formation of the Grignard reagent. When the reaction mixture became warm and began to reflux, the addition rate was regulated to maintain a gentle reflux. After addition was complete, the mixture was heated at reflux for an additional hour. The cooled supernatant solution was transferred via cannula to an addition funnel and added dropwise (over 2.5 hr) to a solution of phenylglyoxal (11.7 g, 87 mmol) in THF (300 mL) at −30° C. under argon. The reaction mixture was gradually warmed to 0° C. over 1 hr and stirred for another 30 min. The resulting mixture was poured into a mixture of ice water (800 mL) and ethyl acetate (250 mL). The organic phase was separated and the aqueous phase was extracted with ethyl acetate (3×). The combined organic phases were washed with $H_2O$ (2×), brine and were dried over $MgSO_4$. Evaporation of the solvent gave 48.8 g of the crude product as a dark green oily liquid. Flash column chromatography of this liquid (gradient elution with hexane, 1.5:98.5, 3:97, 5:95 ethyl acetate:hexane) afforded 24.7 g (50%) of the benzoin product (LSIMS ($C_{42}H_{69}NO_2$):[M−H]$^+$ 618.6, $^1$H NMR (250 MHz, CDCl$_3$) was consistent with the expected benzoin product. To a solution of the benzoin product from above (24.7 g, 40 mmol) in dry toluene (500 mL) was added sequentially 2-mercaptoethanol (25 g, 320 mmol) and TMSCl (100 mL, 788 mmol). The reaction solution was heated at reflux for 23 hr under argon before being cooled to room temperature. To this was added additional TMSCI (50 mL, 394 mmol); and the reaction solution was heated at reflux for another 3 hr. The resulting solution was cooled, was made basic with cold 2.5N aqueous NaOH and was extracted with $CH_2Cl_2$ (3×). The combined organic layers were washed with saturated aqueous NaHCO$_3$ (2×) and brine, was dried over $Na_2SO_4$ and was concentrated in vacuo to give a brown oily liquid. Preparative column chromatography on silica gel by using a Waters 500 Prep LC system (gradient elution with hexane, 1:99, 2:98 ethyl acetate:hexane) provided 15.5 g (60%) of the C-28 thioxene as a yellow oil (LSIMS ($C_{44}H_{71}NOS$): [M−H]$^+$ 661.6, $^1$H NMR (250 MHz, CDCl$_3$) was consistent with the expected C-28 thioxene product 2-(4-(N,N-di-($C_{14}H_{29}$)-anilino)-3-phenyl thioxene.

Silicon Tetra-t-butyl Phthalocyanine:

Sodium metal, freshly cut (5.0 g, 208 mmol), was added to 300 mL of anhydrous methanol in a two-liter, 3-necked flask equipped with a magnetic stirrer, reflux condenser, a drying tube and a gas bubbler. After the sodium was completely dissolved, 4-t-butyl-1,2-dicyanobenzene (38.64 g, 210 mmol, from TCl Chemicals, Portland Oreg.) was added using a funnel. The mixture became clear and the temperature increased to about 50° C. At this point a continuous stream of anhydrous ammonia gas was introduced through the glass bubbler into the reaction mixture for 1 hr. The reaction mixture was then heated under reflux for 4 hr. while the stream of ammonia gas continued during the course of the reaction, as solid started to precipitate. The resulting suspension was evaporated to dryness (house vacuum) and the residue was suspended in water (400 mL) and filtered. The solid was dried (60° C., house vacuum, $P_2O_5$). The yield of the product (1,3-diiminoisoindoline, 42.2 g) was almost quantitative. This material was used for the next step without further purification. To a one-liter, three-necked flask equipped with a condenser and a drying tube was added the above product (1 8 g, 89 mmol) and quinoline (200 mL, Aldrich Chemical Company, St. Louis Mo.). Silicon tetrachloride (11 mL, 95 mmol, Aldrich Chemical Company) was added with a syringe to the stirred solution over a period of 10 minutes. After the addition was completed, the reaction mixture was heated to 180–185° C. in an oil bath for 1 hr. The reaction was allowed to cool to room temperature and concentrated HCl was carefully added to acidify the reaction mixture (pH 5–6). The dark brown reaction mixture was cooled and filtered. The solid was washed with 100 mL of water and dried (house vacuum, 60° C., $P_2O_5$). The solid material was placed in a 1-liter, round bottom flask and concentrated sulfuric acid (500 mL) was added with stirring. The mixture was stirred for 4 hr. at 60° C. and was then carefully diluted with crushed ice (2000 g). The resulting mixture was filtered and the solid was washed with 100 mL of water and dried. The dark blue solid was transferred to a 1-liter, round bottom flask, concentrated ammonia (500 mL) was added, and the mixture was heated and stirred under reflux for 2 hr., was cooled to room temperature and was filtered. The solid was washed with 50 mL of water and dried under vacuum (house vacuum, 60° C., $P_2O_5$) to give 12 g of product silicon tetra-t-butyl phthalocyanine as a dark blue solid. 3-picoline (12 g, from Aldrich Chemical Company), tri-n-butyl amine (anhydrous, 40 mL) and tri-n-hexyl chlorosilane (11.5 g) were added to 12 g of the above product in a one-liter, three-necked flask, equipped with a magnetic stirrer and a reflux condenser. The mixture was heated under reflux for 1.5 hr. and then cooled to room temperature. The picoline was distilled off under high vacuum (oil pump at about 1 mm Hg) to dryness. The residue was dissolved in $CH_2Cl_2$ and purified using a-silica gel column (hexane) to give 10 g of pure product di-(tri-n-hexylsilyl)-silicon tetra-t-butyl phthalocyanine as a dark blue solid. (LSIMS:$[M-H]^+$ 1364.2, absorption spectra:methanol:674 nm ($\epsilon$180,000) :toluene 678 nm, $^1$H NMR (250 MHz, $CDCl_3$):δ:–2.4(m, 12H), –1.3(m, 12H), 0.2–0.9 (m, 54H), 1.8(s, 36H), 8.3(d, 4H) and 9.6 (m, 8H) was consistent with the above expected product.

Hydroxypropylaminodextran: (1 $NH_2$/7 glucose) was prepared by dissolving Dextran T-500 (Pharmacia, Uppsala, Sweden) (50 g) in 150 mL of $H_2O$ in a 3-neck round-bottom flask equipped with mechanical stirrer and dropping funnel. To the above solution was added 18.8 g of Zn $(BF_4)_2$ and the temperature was brought to 87° C. with a hot water bath. Epichlorohydrin (350 mL) was added dropwise with stirring over about 30 min while the temperature was maintained at 87–88° C. The mixture was stirred for 4 hr while the temperature was maintained between 80° C. and 95° C., then the mixture was cooled to room temperature. Chlorodextran product was precipitated by pouring slowly into 3 L of methanol with vigorous stirring, recovered by filtration and dried overnight in a vacuum oven.

The chlorodextran product was dissolved in 200 mL of water and added to 2 L of concentrated aqueous ammonia (36%). This solution was stirred for 4 days at room temperature, then concentrated to about 190 mL on a rotary evaporator. The concentrate was divided into two equal batches, and each batch was precipitated by pouring slowly into 2 L of rapidly stirring methanol. The final product was recovered by filtration and dried under vacuum.

Hydroxypropylaminodextran (1 $NH_2$/7 glucose), prepared above, was dissolved in 50 mM MOPS, pH 7.2, at 12.5 mg/mL. The solution was stirred for 8 hr at room temperature, stored under refrigeration and centrifuged for 45 min at 15,000 rpm in a Sorvall RC-5B centrifuge immediately before use to remove a trace of solid material. To 100 mL of this solution was added 23.1 mg of Sulfo-SMCC in 1 mL of water. This mixture was incubated for 1 hr at room temperature and used without further purification.

N-phenyl Oxazine (NPhe):

The N-phenyl oxazine was prepared by a procedure similar to that described in U.S. Pat. No. 5,578,498 (Singh, et al.) for the preparation of compound 16. The relevant disclosure of the above patent is incorporated herein by reference.

Particle Dyeing

Preparation of N-phenyl Oxazine (N-Phe) Particles

Microgon setup: A Microgon was assembled as described in the MiniKros lab system manual page 8–10. A 0.1 micron module was used operated between about 5–10 psi. The Microgon apparatus was with ethanol (200 proof).

Setup of apparatus:

1. An oil bath was heated to 95° C.±1.0° C. A three-necked 1 liter roundbottom flask (rbf) equipped with a digital Cafeama mechanical stirrer from the middle neck was immersed into the oil bath.

2. Addition of particles: 200 ml±5.0 ml of latex particles were added to the rbf by means of a measuring cylinder, which was washed with 2×30 ml of ethoxyethanol (ee) and the contents were transferred to the rbf. To the flask was added 20±5 ml of 0.1 N sodium hydroxide. The particles were stirred at 330 rpm at 95° C. for 20 minutes.

3. Addition of N-Phe: N-Phe (1.93 gram, 5.4 mmol) was dissolved in 85 ml of ethoxyethanol and the resulting solution was added to the particles dropwise over 85–100 minutes at a constant addition rate of approximately 1.0 ml per minute. The particles were stirred for 5 minutes, and 6.0 ml of 0.1 N sodium hydroxide and 30 ml of deionized water were added over 10 minutes. The particles were stirred for 5 minutes.

4. Addition of Rubrene: Rubrene (480 mg, 0.9 mmol) was dissolved in 200 ml of 1,2-dimethoxyethane and was then added with stirring to the above particles over 70–90 minutes. Rate of addition was 3.0 ml per minute. Next, 30 ml of 0.1 N sodium hydroxide and 120 ml of 0.1 N sodium hydroxide and 120 ml of deionized water were added to the particles over 30 minutes and the medium was stirred for 10 minutes. The medium was cooled to 40° C. over 1 hour with stirring. The particles were subjected to filtration on Microgon apparatus using a 43 micron (Tetko) filter (from Tetko Inc. Briarcliff Manor, N.Y.).

Preparation of Thioxene—Diphenylethynyl Anthracene (DPA) Particle

Microgon setup: A Microgon was assembled as described in the MiniKros lab system manual page 8–10. A 0.1 micron module was used operated between about 5–10 psi. The Microgon apparatus was with ethanol (200 proof).

Setup of Apparatus:

1. An oil bath was heated to 95° C.±1.0° C. A three-necked 1 liter roundbottom flask (rbf) equipped with a digital Cafeama mechanical stirrer from the middle neck was immersed into the oil bath.

2. Addition of particles: 200 ml±5.0 ml of latex particles were added to the rbf by means of a measuring cylinder, which was washed with 2×30 ml of ethoxyethanol (ee) and the contents were transferred to the rbf. To the flask was added 20±5 ml of 0.1 N sodium hydroxide. The particles were stirred at 330 rpm at 95° C. for 20 minutes.

3. Addition of C-28 thioxene: 3.6 grams of C-28 thioxene was dissolved in 85 ml of ethoxyethanol and the resulting solution was added to the particles dropwise over 85–100 minutes at a constant addition rate of approximately 1.0 ml per minute. The particles were stirred for 5 minutes and 6.0 ml of 0.1 N sodium hydroxide and 30 ml of deionized water were added over 10 minutes. The particles were stirred for 5 minutes.

4. Addition of DPA: DPA (341 mg, 0.9 mmol) was dissolved in 200 ml of 1,2-dimethoxyethane and was then added with stirring to the above particles over 70–90 minutes. Rate of addition was 3.0 ml per minute. Next, 30 ml of 0.1 N sodium hydroxide and 120 ml of 0.1 N sodium hydroxide and 120 ml of deionized water were added to the particles over 30 minutes and the medium was stirred for 10 minutes. The medium was cooled to 40° C. over 1 hour with stirring. The particles were subjected to filtration on Microgon apparatus using a 43 micron (Tetko) filter (from Tetko Inc. Briarcliff Manor, N.Y.).

Oligonucleotide Bound Sensitizer Particles:

The oligonucleotide was immobilized on the surface of the above particles in the following manner. Aminodextran (500 mg) was partially maleimidated by reacting it with sulfo-SMCC (157 mg, 10 mL $H_2O$). The sulfo-SMCC was added to a solution of the aminodextran (in 40 mL, 0.05 M $Na_2HPO_4$, pH 7.5) and the resulting mixture was incubated for 1.5 hr. The reaction mixture was then dialyzed against MES/NaCl (2×2 L, 10 mM MES, 10 mM NaCl, pH 6.0, 4° C.). The maleimidated dextran was centrifuged at 15,000 rpm for 15 minutes and the supernatant collected. The supernatant dextran solution (54 mL) was then treated with imidazole (7 mL of 1.0 M solution) in MES buffer (pH 6.0) and into this stirred solution was added the stained photosensitizer particles (10 mL of 10 mg/mL). After stirring for 10 minutes the suspension was treated with EDAC (7 mmol in 10 mM pH 6.0 MES) and the suspension stirred for 30 minutes. After this time, SurfactAmps® (Pierce Chemical Company) Tween-20 (10%, 0.780 mL) was added to the reaction mixture for a final concentration of 0.1%. The particles were then centrifuged at 15,000 rpm for 45 minutes and the supernatant discarded. The pellet was resuspended in MES/NaCl (pH 6.0,10 mM, 100 mL) by sonication. Centrifugation at 15,000 rpm for 45 minutes, followed by pellet resuspension after discarding the supernatant, was performed twice. The maleimidated dextran photosensitizer particles were stored in water as a 10 mg/mL suspension.

Thiolated oligonucleotide (oligonucleotide bearing a 5'-bis(6-hydroxyethyidisulfide) group) (Oligos Etc.) was dissolved in water at a concentration of 0.49 mM. To 116 μL of this solution was added 8.3 μL of 3.5 M sodium acetate, pH 5.3 and 8.9 μL of tris(carboxyethyl)phosphine (20 mM). After 30 minutes incubation at room temperature, 548 μL of cold ethanol. Was added and the mixture was maintained at about 20° C. for 1.5 hour. The precipitated oligonucleotide was recovered by centrifugation for 2 min. at 15,000 rpm in an Eppendorf centrifuge, then dissolved in 37.5 μL of 5 mM sodium phosphate, 2 mM EDTA, pH 6.

An aliquot of the maleimidated beads prepared above containing 22 mg beads was centrifuged for 30 min. at about 37,000 g, and the pellet was resuspended in 96 μL of 0.26 M NaCl, 0.05% Tween-20, 95 mM sodium phosphate, and 0.95 mM EDTA, pH7. The thiolated oligonucleotide was added and the mixture was maintained at 37° C. for 64 hours under argon. A 10 μL aliquot of sodium thioglycolate was added and incubation was continued for 2 hours at 37° C. Water was added to a total volume of 1 mL, and the beads were recovered by centrifugation, then resuspended in 5 mL of 0.1 M NaCl, 0.17 M glycine, 10 mg/mL BSA, 1 mM EDTA, 0.1% Tween-20, and 0.5 mg/mL Calf thymus DNA (Sigma Molecular Biology grade), pH 9.2. After three hours, the beads were recovered and washed three times by centrifugation, twice in buffer A and once in standard PCR buffer. The product was stored refrigerated in PCR buffer. Buffer A contained 0.1 M Tris base (J. T. Baker Chemical Co.), 0.3 M NaCl (Mallinckrodt), 25 mM EDTA $Na_2$ $H_2O$ (Sigma Chemical Co.), 0.1% BSA (Sigma Chemical Co.), 0.1% dextran (Pharmacia), HBR-1 (Scantibodies), 0.05% Kathon and 0.01% gentamycin sulfate (GIBCO) prepared by dissolving and adjusting pH to 8.20 with concentrated HCL and made up to 10 L with distilled water.

A similar procedure was used for the preparation of oligonucleotide bound chemiluminescer particles The above procedure may be modified in a manner similar to that described by Ullman, et al., Proc. Natl. Acad. Sci. USA (1994) 91:5426–5427 at column 1 of page 5427.

Example 1

Target HIV RNA (obtained from Organon Teknika, Boxtel, Netherlands) was amplified by the isothermal NASBA amplification procedure. The NASBA Amplification Kit of Organon Teknika was employed. Target RNA, referred to below as WT) at various initial input (number of molecules per reaction) was amplified in the presence of reference RNA, at known number of molecules. The reference RNA molecules, referred to below as $Q_a$) were engineered (by Organon Teknika) to be homologous to the target RNA except for an internal sequence of 21 nucleotides. This sequence in the reference RNA was 63 nucleotides from the 3'-end thereof and was complementary to the sequence in the third oligonucleotide probe as set forth below. The corresponding sequence in the target RNA was complementary to the sequence in the second oligonucleotide probe as set forth below. A sequence in both the target and reference RNA that was 29 nucleotides from the 3' end was complementary to a sequence in the first oligonucleotide probe or common probe.

The above design of the reference RNA ensures amplification of the reference and target RNA by the same NASBA primers and enzyme at equal amplification efficiency for target and reference RNA. The sequence of the target and reference RNA was as described by the manufacturer in the J. of Virological Methods (1993) 43:177–188.

A homogenous chemiluminescence detection method as described above was used to generate signals for determination. Chemiluminescence signal was produced when a pair of probes became bound to the target RNA analyte, one of which was bound to a singlet oxygen-producing particle, the sensitizer particle, and the other of which was bound to a particle dyed with a specific acceptor dye. These probes are referred to herein as particle detection probes. The particle detection probes included a first oligonucleotide detection probe that comprised a sequence that was complementary to a sequence in the first oligonucleotide probe indicated by underlining in the sequence below. A particle with which a sensitizer was associated was attached at the 3'-end of the first oligonucleotide detection probe. A second oligonucleotide detection probe comprised a sequence that was complementary to a sequence in the second oligonucleotide probe indicated by underlining in the sequence below.

DPA dyed particles were attached at the 3'-end of the second oligonucleotide detection probe. A third oligonucleotide detection probe comprised a sequence that was complementary to a sequence in the third oligonucleotide probe indicated by underlining in the sequence below. N-PHE dyed particles were attached at the 3'-end of the third oligonucleotide detection probe. The particle detection probes became bound to the respective first, second or third oligonucleotide probes used in this example, where the binding was non-covalent and based on the hybridization of a sequence of the particle detection probes, either a 3'- or 5'-oligonucleotide tail, to a complementary sequence in the respective first, second or third oligonucleotide probes. Chemiluminescence signals produced by complexes of the common sensitizer particle, with each of the specific chemiluminescer particles, were specifically detected.

First Oligonucleotide Probe:
5'$(dT)_{20}$TGTTAAAAGAGACCATCAATGAGGA 3' (SEQ ID NO:1)
Second Oligonucleotide Probe:
5'$(TACT)_5$GCTGCAGAATGGGATAGA3' (SEQ ID NO:2)
Third Oligonucleotide Probe:
5'GATGACAGTCGCATGCAG$(CTAT)_5$ 3' (SEQ ID NO:3) All probes were 3'—amino blocked and gel-purified by the manufacturer, namely, Oligos Etc. The underlined portions of the probes represent the sequences of 20 nucleotides that are complementary to the particle detection probes.

The sequence of the particle detection probe bound to sensitizer particles had the sequence $dA_{24}$.

The sequence of the particle detection probe bound to chemiluminescent particles dyed with N-PHE: 5' $(ATAG)_6$.

The sequence of the particle probe bound to the chemiluminescent dyed with DPA: 5' $(ATGA)_6$.

RNA amplification of the test and reference RNA was carried out in mixtures containing all probes, detection particles and amplification reagents. The amplification reagents used were provided by the manufacturer (Organon Teknika). The lyophilized NASBA reagent Accusphere™ was reconstituted as directed. The reagent mixture includes all primers, NTPs, $MgCl_2$ and buffer components. The target and reference RNA, the first, second and third oligonucleotide probes and corresponding particle detection probes were added to the reconstituted reaction mixture. The concentration of the first oligonucleotide probe was 25 nM and the concentration of the second and third oligonucleotide probes were at final concentration of 25 nM. The concentration of the particle detection probes were at final concentration of 1 μg per reaction. Target and reference RNA molecules, at known number of molecules, were added (2 μl) to the corresponding amplification tubes. The total volume of the initial reaction mixtures, including the target and reference RNA, was 15 μl. The mixtures were overlaid with 20 μl white, light mineral oil (Aldrich Chemical Co.) and incubated at 65° C. for 5 min. Following incubation at 41° C. for 10 min., the mixture of enzymes (5 μl from Organon Teknika) was added.

Following addition of the enzyme mixture, the amplification reactions were carried out by incubation at 41° C. for 60 min. The signals were read using the following program: Illumination for 0.1 sec. and read for 2.0 sec. (380–440 nm filter), followed by illumination for 0.5 sec., delay for 30 sec. and read for 10 sec. (550–660 nm filter). All measurements were carried out using a manual reader built in-house. This reader is similar to conventional readers except that it had a mechanism for fast filter change. The results are summarized in Table 2.

TABLE 2

| Target | WT/Qa | Corrected signal DPA (WT) | Ratio N-Phe* (Qa) | Input/ 1.89** | Signal |
|---|---|---|---|---|---|
| 0/0 | | | | | |
| 100/0 | | 34471 | −30 | | |
| 50/0 | | 23321 | −14 | | |
| 0/100 | | 47 | 22540 | | |
| 50/100 | | 19240 | 13559 | 0.5 | 0.72 |
| 100/100 | | 24875 | 12445 | 1 | 1.00 |
| 500/100 | | 26787 | 2095 | 5 | 5.00 |
| 1000/10 0 | | 36528 | 292 | 10 | 14.82 |

*Corrected N-Phe signal = $[S-B_{N-Phe}$ minus $S-B_{DPA}] \times 0.028$ wherein S-B is Signal-Background. The correction factor 0.028 reflects 2.8% cross-over of DPA signal into the N-Phe signal channel.
**The ratio of corrected signal from test (WT) and reference (Qa) was divided by 1.89, to reflect the difference of chemiluminescence signal detection.

In summary, the above results demonstrate that the ratio of concentrations of the target RNA sequences can be measured by measuring the corrected ratio of the chemiluminescent signals.

Example 2

NASBA amplification and quantification of an HIV target in sample was carried out as described in Example 1. Known input amount of the test HIV target (WT) was mixed with known input amount of reference target, Qa. 2 μl of the mixture of targets was added to 13 μl of reaction mixture containing the primers, dNTPs and NTPs, the NASBA buffer, the three probes and the chemiluminescer beads and the photosensitizer beads. The oligonucleotide chemiluminescer beads were dyed with DPA, for the WT specific probe, and N-PHE, for the Qa specific probe. 1 μg of each of the chemiluminescer beads was used per assay. The reaction mixture contained 0.25 μg (per assay) of the sensitizer beads (specific for binding of the common probe). The following probes were used in the example: Oligonucleotide SEQ ID NO: 1(OB-1 common probe) at 12.5 nM; SEQ ID NO:4 (EF-4; specific for WT) at 25 nM; and SEQ ID NO 5 (EF-7; specific for Qa) at 25 nM.

The oligonucleotides EF-4 and EF-7 were as follows:
5' GCTGCAGMTGGGATAGA$(TACT)_5$ 3' SEQ ID NO:4 (EF-4)
5' GCTGCAGACAGTGTAGATA$(CTAT)_5$ 3' SEQ ID NO:5 (EF-7)
All sequences were blocked at the 3'-end by the manufacturer and gel purified. The 20 nucleotide tails on the oligonucleotide probes were complementary to the 24 nucleotide sequence present on the oligonucleotide bound chemiluminescer particles.

20 μl of mineral oil was added to each reaction tube and the tubes were incubated at 65° C. for 5 minutes followed by incubation at 41° C. for 10 minutes. 5 μl of a mixture of the amplification enzymes was added to each reaction tube and amplification was carried out for 90 minutes at 41° C. The signals were read as follows: Three cycles of 1 sec illumination and 0.5 sec read, followed by 30 sec delay and 10 sec read.

The obtained signals for the DPA and N-PHE chemiluminescence were corrected as follows: The background signal was subtracted and the obtained signal was corrected using a correction factor calculated from signal obtained with the individual targets. This correction was required due to cross over of the signal from one chemiluminescence into the other. The results are shown in Table 3 below.

TABLE 3

| Input Number of target molecules WT/Qa | Corrected Signal WT | Corrected Signal Qa | Ratio Input | Ratio Calc. Signal WT/Qa/1.5 |
|---|---|---|---|---|
| 1e5/5e3 | 47404 | 1348 | 20 | 23.44 |
| 5e4/5e3 | 49879 | 3562 | 10 | 9.34 |
| 5e4/5e3 | 51865 | 5609 | 10 | 6.16 |
| 5e3/5e3 | 40364 | 26688 | 1 | 1.01 |
| 5e3/5e3 | 36936 | 24148 | 1 | 1.02 |
| 5e2/5e3 | 14846 | 56322 | 0.1 | 0.18 |
| 5e2/5e3 | 13187 | 55392 | 0.1 | 0.16 |
| 2.5e2/5e | 962 | 67457 | 0.05 | 0.01 |
| 0/0 | 0 | 0 | | |
| 5e3/0 | 49174 | 274 | | |
| 0/5e3 | 1 | 63622 | | |

The above discussion includes certain theories as to mechanisms involved in the present invention. These theories should not be construed to limit the present invention in any way, since it has been demonstrated that the present invention achieves the results described.

The above description and examples fully disclose the invention including preferred embodiments thereof. Modifications of the methods described that are obvious to those of ordinary skill in the art such as molecular biology and related sciences are intended to be within the scope of the following claims.

What is claimed is:

1. A method for detecting the amount of a target polynucleotide in a sample, said method comprising:
   (a) providing in combination in a medium (i) a sample suspected of containing said target polynucleotide, said target polynucleotide being in single stranded form, (ii) a reference polynucleotide comprising a sequence that is common with a sequence of said target polynucleotide, and (iii) a predetermined amount of an oligonucleotide probe that has a sequence that hybridizes with said sequence that is common;
   (b) subjecting said combination to conditions for amplifying said target polynucleotide and said reference polynucleotide wherein said conditions permit formation of substantially non-dissociative complexes of said target polynucleotide and said reference polynucleotide, respectively, with said oligonucleotide probe and wherein said predetermined amount of said oligonucleotide probe is less than the expected amount of said amplified target polynucleotide,
   (c) determining the ratio of the amount of said complex of said target polynucleotide with said oligonucleotide probe to the amount of said complex of said reference polynucleotide with said oligonucleotide probe, and
   (d) relating said ratio to said known amount of said reference polynucleotide to determine the amount of said target polynucleotide in said sample.

2. The method of claim 1 wherein a signal is produced by the complex of said target polynucleotide with said oligonucleotide probe wherein said signal is different from a signal produced by the complex of said reference polynucleotide with said oligonucleotide probe and the ratio of said signals is related to the amount of said reference polynucleotide to determine the amount of said target polynucleotide in said sample.

3. The method of claim 1 wherein said amplification is selected from the group consisting of NASBA, 3SR, SDA and amplifications utilizing Qβ-replicase.

4. The method of claim 1 wherein said polynucleotide is DNA.

5. The method of claim 1 wherein said polynucleotide is RNA.

6. A method for detecting the amount of a target polynucleotide in a sample, said method comprising:
   (a) providing in combination in a medium (i) a sample suspected of containing said target polynucleotide, said target polynucleotide being in single stranded form, (ii) predetermined amounts of one or more reference polynucleotides, each of said reference polynucleotides comprising a first sequence that is common with a first sequence of said target polynucleotide and a second sequence that is different from a second sequence of said target polynucleotide, (iii) a predetermined amount of a first oligonucleotide probe that has a sequence that hybridizes with said sequence that is common, (iv) a second oligonucleotide probe that has a sequence that hybridizes only with said second sequence of said target polynucleotide, and (v) one or more third oligonucleotide probes, each of said third oligonucleotide probes having a sequence that hybridizes only with a respective second sequence of one of said reference polynucleotide;
   (b) subjecting said combination to isothermal conditions for amplifying with equal efficiency said target polynucleotide and said one or more reference polynucleotides wherein said conditions permit formation of a substantially non-dissociative first termolecular complex of said target polynucleotide, said first oligonucleotide probe and said second oligonucleotide probe and a substantially non-dissociative second termolecular complex of each of said reference polynucleotide with said first oligonucleotide probe and a respective third oligonucleotide probe and wherein said predetermined amount of said first oligonucleotide probe is less than the expected amount of said amplified target polynucleotide, (c) determining the ratio of the amount of said first termolecular complex to the amount of each of said second termolecular complexes, and (d) relating each of said ratios to the predetermined amount of each of said reference polynucleotides to determine the amount of said target polynucleotide in said sample.

7. The method of claim 6 wherein said first termolecular complex has a first signal producing system and each of said second termolecular complexes has a second signal producing system wherein a signal produced by said first signal producing system is different from a signal produced by each of said second signal producing systems.

8. The method of claim 7 wherein the ratio of said signals is determined and related to the predetermined amount of said reference polynucleotide to determine the amount of said target polynucleotide in said sample.

9. The method of claim 7 wherein said signal producing systems comprise labels selected from the group consisting of a luminescent energy donor and acceptor pair, a singlet oxygen generator and chemiluminescent reactant pair, and an enzyme pair wherein a product of the first enzyme serves as a substrate for the second enzyme.

10. The method of claim 6 wherein said amplification is selected from the group consisting of NASBA, 3SR, SDA and amplifications utilizing Qβ-replicase.

11. The method of claim 6 wherein said polynucleotide is DNA.

12. The method of claim 6 wherein said polynucleotide is RNA.

13. The method of claim 6 wherein one of said first and second oligonucleotide probes is labeled with a sensitizer.

14. The method of claim 6 wherein one of said first and second oligonucleotide probes is labeled with a chemiluminescent compound.

15. The method of claim 6 wherein said predetermined amount of said first oligonucleotide probe is about 50-fold less than the expected amount of said amplified target polynucleotide.

16. A method for detecting the amount of a target polynucleotide in a sample, said method comprising:

(a) providing in combination in a medium (i) a sample suspected of containing said target polynucleotide, said target polynucleotide being in single stranded form, (ii) predetermined amounts of one or more reference polynucleotides, each of said reference polynucleotides comprising a first sequence that is common with a first sequence of said target polynucleotide and a second sequence that is different from a second sequence of said target polynucleotide, (iii) a predetermined amount of a first oligonucleotide probe that has a sequence that hybridizes with said sequence that is common wherein said first oligonucleotide probe has, or is capable of having, a sensitizer attached thereto, (iv) a second oligonucleotide probe that has a sequence that hybridizes only with said second sequence of said target polynucleotide wherein said second oligonucleotide probe has, or is capable of having, a first chemiluminescent compound attached thereto, and (v) one or more third oligonucleotide probes, each having a sequence that hybridizes only with a respective second sequence of one of said reference polynucleotides wherein each of said third oligonucleotide probes has, or is capable of having, a second chemiluminescent compound attached thereto, said first and said second chemiluminescent compounds differ in signal produced when activated by said photosensitizer; said second chemiluminescent compound being different for each of said third oligonucleotide probes, (b) subjecting said combination to isothermal conditions for amplifying with equal efficiency said target polynucleotide and each of said reference polynucleotide wherein said conditions permit formation of a substantially non-dissociative first termolecular complex of said target polynucleotide, said first oligonucleotide probe and said second oligonucleotide probe and a substantially non-dissociative second termolecular complex of each of said reference polynucleotides with said first oligonucleotide probe and a respective third oligonucleotide probe and wherein said predetermined amount of said first oligonucleotide probe is less than the expected amount of said amplified target polynucleotide, (c) determining the ratio of the amount of said signal produced by said first termolecular complex to the amount of signal produced by each of said second termolecular complexes, and (d) relating each of said ratios to the amount of each respective reference polynucleotide to determine the amount of said target polynucleotide in said sample.

17. The method of claim 16 wherein said chemiluminescent compounds are each independently selected from the group consisting of enol ethers, enamines, 9-alkylidene-N-alkylacridans, arylvinylethers, dioxenes, arylimidazoles, 9-alkylidene-xanthanes and lucigenin.

18. The method of claim 16 wherein said sensitizer is a photosensitizer.

19. The method of claim 18 wherein said photosensitizer is selected from the group consisting of methylene blue, rose bengal, porphyrins and phthalocyanines.

20. The method of claim 16 wherein said amplification is selected from the group consisting of NASBA, 3SR, SDA and amplifications utilizing Qβ-replicase.

21. The method of claim 16 wherein said polynucleotide is DNA.

22. The method of claim 16 wherein said polynucleotide is RNA.

* * * * *